United States Patent
Freier (12)

(10) Patent No.: US 6,440,737 B1
(45) Date of Patent: Aug. 27, 2002

(54) ANTISENSE MODULATION OF CELLULAR APOPTOSIS SUSCEPTIBILITY GENE EXPRESSION

(75) Inventor: Susan M. Freier, San Diego, CA (US)

(73) Assignee: ISIS Pharmaceuticals, Inc., Carlsbad, CA (US)

(*) Notice: Subject to any disclaimer, the term of this patent is extended or adjusted under 35 U.S.C. 154(b) by 0 days.

(21) Appl. No.: 09/705,299

(22) Filed: Nov. 1, 2000

(51) Int. Cl.[7] .................. C12Q 1/68; C07H 21/04; C12N 15/85
(52) U.S. Cl. .................. 435/375; 435/6; 435/91.1; 435/325; 435/366; 536/23.1; 536/24.31; 536/24.33; 536/24.5
(58) Field of Search .................. 435/6, 325, 366, 435/375; 536/23.1, 24.5, 25.3; 514/44

(56) References Cited

U.S. PATENT DOCUMENTS

| | | | |
|---|---|---|---|
| 5,759,782 A | 6/1998 | Pastan et al. ............. | 435/6 |
| 5,801,154 A | * 9/1998 | Baracchini et al. ............. | 514/44 |
| 5,951,455 A | * 9/1999 | Cowsert ............. | 495/375 |
| 6,072,031 A | 6/2000 | Pastan et al. ............. | 530/350 |

FOREIGN PATENT DOCUMENTS

WO  WO 96/40713  12/1996

OTHER PUBLICATIONS

Afford et al., Apoptosis, Mol. Pathol., 2000, 53: 55–63 Böni et al., Expression of the proliferation and apoptosis–associated CAS protein in benign and malignant cutaneous melanocytic lesions, The American Journal of Dermatopathology, 1999, 21: 125–128.

Brinkmann, CAS, the human homoloque of the yeast chromoson–segregation gene CSE1, proliferation, apoptosis, and cancer, Am. J. Hum. Genet., 1998, 62: 509–513.

Brinkmann et al., Tissue–specific alternative splicing of the CSE1L/CAS (cellular apoptosis susceptibility) gen, Genomics, 1999, 58: 41–49.

Brinkmann et al., Cloning and Characterization of a cellular apoptosis susceptibility gene, the human homologue to the yeast chromosome segregation gene CSE1, Proc. Natl. Acad. Sci. U .S. A., 1995, 92: 10427–10431.

Brinkmann et al., Role of CAS, a human homologue to the yeast chromsome segregation gene CSE1, in toxin and tumor necrosis factor mediated apoptosis, Biochemistry, 1996, 35: 6891–6899.

Brinkmann et al., The human CAS (cellular apoptosis susceptibility) gene mapping on chromosome 20q13 is amplified in BT474 breast cancer cells and part of aberrant chromosomes in breast and colon cancer cell lines, Genome Research, 1996, 6: 187–194.

Kutay et al., Export of importin alpha from the nucleus is mediated by a specific nuclear transport factor [see comments], cell, 1997, 90:1061–1071.

Ogrtyzko et al., Antisense inhibition of CAS, the human homologne of the yeast chromosom segregation gene CSE1, interferes with mitosis in HeLa cells, Biochemistry, 1997, 36: 9493–9500.

Scherf et al., The hCSE1/CAS protein is0 phosphorylated by HeLa extracts and MEK–1: MEK–1 phosphorylation may modulate the intracellular localization of CAS, Biochemical and Biophysical Research Comminications, 1998, 250:623–628.

Scherf et al., The human CAS protein which is homologous to the CSE1 yeast chromosome segregation gene product is associated with microtubules and mitotic spindle, Proc. Natl. Acad. Sci. U. S. A., 1996, 93:2670–2674.

Wellman et al., Localization of the cell proliferation and apoptosis–associated CAS protein in lymphiod neoplasms, American Journal of Pathology, 1997, 150: 25–30.

* cited by examiner

Primary Examiner—John L. LeGuyader
Assistant Examiner—Mary Schmidt
(74) Attorney, Agent, or Firm—Licata & Tyrrell P.C.

(57) ABSTRACT

Antisense compounds, compositions and methods are provided for modulating the expression of cellular apoptosis susceptibility gene. The compositions comprise antisense compounds, particularly antisense oligonucleotides, targeted to nucleic acids encoding cellular apoptosis susceptibility gene. Methods of using these compounds for modulation of cellular apoptosis susceptibility gene expression and for treatment of diseases associated with expression of cellular apoptosis susceptibility gene are provided.

26 Claims, No Drawings

ANTISENSE MODULATION OF CELLULAR APOPTOSIS SUSCEPTIBILITY GENE EXPRESSION

FIELD OF THE INVENTION

The present invention provides compositions and methods for modulating the expression of cellular apoptosis susceptibility gene. In particular, this invention relates to compounds, particularly oligonucleotides, specifically hybridizable with nucleic acids encoding cellular apoptosis susceptibility gene. Such compounds have been shown to modulate the expression of cellular apoptosis susceptibility gene.

BACKGROUND OF THE INVENTION

Apoptosis, or programmed cell death, is a naturally occurring process that has been strongly conserved during evolution to prevent uncontrolled cell proliferation. This form of cell suicide plays a crucial role in ensuring the development and maintenance of multicellular organisms by eliminating superfluous or unwanted cells. However, if this process goes awry becoming overstimulated, cell loss and degenerative disorders including neurological disorders such as Alzheimers, Parkinsons, ALS, retinitis pigmentosa and blood cell disorders can result. Stimuli which can trigger apoptosis include growth factors such as tumor necrosis factor (TNF), Fas and transforming growth factor beta (TGFβ), neurotransmitters, growth factor withdrawal, loss of extracellular matrix attachment and extreme fluctuations in intracellular calcium levels (Afford and Randhawa, Mol. Pathol., 2000, 53, 55–63).

Alternatively, insufficient apoptosis, triggered by growth factors, extracellular matrix changes, CD40 ligand, viral gene products neutral amino acids, zinc, estrogen and androgens, can contribute to the development of cancer, autoimmune disorders and viral infections (Afford and Randhawa, Mol. Pathol., 2000, 53, 55–63). Consequently, apoptosis is regulated under normal circumstances by the interaction of gene products that either induce or inhibit cell death and several gene products which modulate the apoptotic process have now been identified.

Cellular apoptosis susceptibility gene (also known as CAS, CSE1 and CSP) is the human homolog of the yeast chromosome segregation gene, CSE1, and has been simultaneously implicated in the regulation of mitosis, apoptosis and cellular proliferation (Brinkmann et al., Biochemistry, 1996, 35, 6891–6899; Scherf et al., Proc. Natl. Acad. Sci. U. S. A., 1996, 93, 2670–2674).

CAS was first identified in a screen for genes that affect the sensitivity of breast cancer cells toward toxins used in experimental cancer therapy. In these screens cellular apoptosis susceptibility gene was isolated as antisense cDNA fragments that rendered MCF-7 breast cancer cells resistant to cell death induced by exotoxins, exotoxin-derived immunotoxins, diptheria toxin and tumor necrosis factor (Brinkmann et al., Proc. Natl. Acad. Sci. U. S. A., 1995, 92, 10427–10431; Ogryzko et al., Biochemistry, 1997, 36, 9493–9500). Characterization of the protein has since revealed that the cellular apoptosis susceptibility gene is highly expressed in other cancer cells including lymphoid neoplasms (Wellmann et al., American Journal of Pathology, 1997, 150, 25–30), benign and malignant cutaneous melanocytic lesions (Böni et al., The American Journal of Dermatopathology, 1999, 21, 125–128), and colon cancer cell lines (Brinkmann, Am. J. Hum. Genet., 1998, 62, 509–513; Brinkmann et al., Genome Research, 1996, 6, 187–194).

It has been determined that cellular apoptosis susceptibility gene undergoes alternative splicing in a tissue—and development-specific manner (Brinkmann et al., Genomics, 1999, 58, 41–49). Northern blot analyses have shown that the predominant transcript in proliferating tissues is a 3147 nucleotide transcript, while a larger transcripts can be detected in fetal and adult brain and smaller transcripts can be detected in trachea, liver and some cancers (Brinkmann et al., Genomics, 1999, 58, 41–49). The protein and nucleic acid sequences of the human cellular apoptosis susceptibility gene are disclosed in U.S. Pat. No. 5,759,782 and its corresponding PCT publication WO 96/40713 and U.S. Pat. No. 6,072,031, respectively (Pastan and Brinkmann, 2000; Pastan and Brinkmann, 1996; Pastan and Brinkmann, 1998). Also disclosed are antibodies to the protein, protein fragments and an isolated single-stranded antisense DNA sequence consisting of nucleotides 2100–2536 of the human cellular apoptosis susceptibility gene (Pastan and Brinkmann, 1996; Pastan and Brinkmann, 1998).

The human cellular apoptosis susceptibility gene is located on chromosome 20q13 and is amplified in BT474 breast cancer cells (Brinkmann et al., Genome Research, 1996, 6, 187–194). This chromosomal location harbors a remarkable degree of instability in various tumors and amplification in this region is observed frequently in aggressive types of breast cancers (Brinkmann et al., Genome Research, 1996, 6, 187–194).

Cellular apoptosis susceptibility gene has also been shown to mediate export of importin-α from the nucleus (Kutay et al., Cell, 1997, 90, 1061–1071). Importin-α is the nuclear import receptor for nuclear localization signal-containing proteins. This interaction, which is regulated by phosphorylation events, requires the presence of RanGTP to form a ternary complex; and it has been suggested that deregulation of importin transport can cause cell cycle defects (Kutay et al., Cell, 1997, 90, 1061–1071; Scherf et al., Biochemical and Biophysical Research Communications, 1998, 250, 623–628).

Collectively, these data suggest that modulation of cellular apoptosis susceptibility gene would render opportunity to treat patients with various cancers and deregulated apoptotic pathologic conditions.

Strategies aimed at modulating cellular apoptosis susceptibility gene function have involved the use of antibodies and antisense expression vectors but currently, there are no known therapeutic agents which effectively inhibit the synthesis of cellular apoptosis susceptibility gene. Consequently, there remains a long felt need for agents capable of effectively inhibiting cellular apoptosis susceptibility gene function.

Antisense technology is emerging as an effective means for reducing the expression of specific gene products and may therefore prove to be uniquely useful in a number of therapeutic, diagnostic, and research applications for the modulation of cellular apoptosis susceptibility gene expression.

Currently there exists a need to identify methods of modulating apoptosis for the therapeutic treatment of human diseases and it is believed that cellular apoptosis susceptibility gene modulators will be integral to these methods. The present invention, therefore, provides compositions and methods for modulating cellular apoptosis susceptibility gene expression, including modulation of alternatively spliced forms of cellular apoptosis susceptibility gene.

SUMMARY OF THE INVENTION

The present invention is directed to compounds, particularly antisense oligonucleotides, which are targeted to a nucleic acid encoding cellular apoptosis susceptibility gene, and which modulate the expression of cellular apoptosis susceptibility gene. Pharmaceutical and other compositions comprising the compounds of the invention are also provided. Further provided are methods of modulating the expression of cellular apoptosis susceptibility gene in cells or tissues comprising contacting said cells or tissues with one or more of the antisense compounds or compositions of the invention. Further provided are methods of treating an animal, particularly a human, suspected of having or being prone to a disease or condition associated with expression of cellular apoptosis susceptibility gene by administering a therapeutically or prophylactically effective amount of one or more of the antisense compounds or compositions of the invention.

DETAILED DESCRIPTION OF THE INVENTION

The present invention employs oligomeric compounds, particularly antisense oligonucleotides, for use in modulating the function of nucleic acid molecules encoding cellular apoptosis susceptibility gene, ultimately modulating the amount of cellular apoptosis susceptibility gene produced. This is accomplished by providing antisense compounds which specifically hybridize with one or more nucleic acids encoding cellular apoptosis susceptibility gene. As used herein, the terms "target nucleic acid" and "nucleic acid encoding cellular apoptosis susceptibility gene" encompass DNA encoding cellular apoptosis susceptibility gene, RNA (including pre-mRNA and mRNA) transcribed from such DNA, and also cDNA derived from such RNA. The specific hybridization of an oligomeric compound with its target nucleic acid interferes with the normal function of the nucleic acid. This modulation of function of a target nucleic acid by compounds which specifically hybridize to it is generally referred to as "antisense". The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of cellular apoptosis susceptibility gene. In the context of the present invention, "modulation" means either an increase (stimulation) or a decrease (inhibition) in the expression of a gene. In the context of the present invention, inhibition is the preferred form of modulation of gene expression and mRNA is a preferred target.

It is preferred to target specific nucleic acids for antisense. "Targeting" an antisense compound to a particular nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding cellular apoptosis susceptibility gene. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding cellular apoptosis susceptibility gene, regardless of the sequence(s) of such codons.

It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which is known in the art to refer to the region between the translation initiation codon and the translation termination codon, is also a region which may be targeted effectively. Other target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'—5' triphosphate linkage. The 5' cap region of an MRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA splice sites, i.e., intron-exon junctions, may also be preferred target regions, and are particularly useful in situations where aberrant splicing is implicated in disease, or where an overproduction of a particular mRNA splice product is implicated in disease.

Aberrant fusion junctions due to rearrangements or deletions are also preferred targets. It has also been found that introns can also be effective, and therefore preferred, target regions for antisense compounds targeted, for example, to DNA or pre-mRNA.

Once one or more target sites have been identified, oligonucleotides are chosen which are sufficiently complementary to the target, i.e., hybridize sufficiently well and with sufficient specificity, to give the desired effect.

In the context of this invention, "hybridization" ' means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

Antisense and other compounds of the invention which hybridize to the target and inhibit expression of the target are identified through experimentation, and the sequences of these compounds are hereinbelow identified as preferred embodiments of the invention. The target sites to which these preferred sequences are complementary are hereinbelow referred to as "active sites" and are therefore preferred sites for targeting. Therefore another embodiment of the invention encompasses compounds which hybridize to these active sites.

Antisense compounds are commonly used as research reagents and diagnostics. For example, antisense oligonucleotides, which are able to inhibit gene expression with exquisite specificity, are often used by those of ordinary skill to elucidate the function of particular genes. Antisense compounds are also used, for example, to distinguish between functions of various members of a biological pathway. Antisense modulation has, therefore, been harnessed for research use.

The specificity and sensitivity of antisense is also harnessed by those of skill in the art for therapeutic uses. Antisense oligonucleotides have been employed as therapeutic moieties in the treatment of disease states in animals and man. Antisense oligonucleotide drugs, including ribozymes, have been safely and effectively administered to humans and numerous clinical trials are presently underway. It is thus established that oligonucleotides can be useful therapeutic modalities that can be configured to be useful in treatment regimes for treatment of cells, tissues and animals, especially humans.

In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 50 nucleobases (i.e. from about 8 to about 50 linked nucleosides). Particularly preferred antisense compounds are antisense oligonucleotides, even more preferably those comprising from about 12 to about 30 nucleobases. Antisense compounds include ribozymes, external guide sequence (EGS) oligonucleotides (oligozymes), and other short catalytic RNAs or catalytic oligonucleotides which hybridize to the target nucleic acid and modulate its expression.

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'–5' linkages, 2'–5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., *Science,* 1991, 254, 1497–1500.

Most preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE) (Martin et al., *Helv. Chim. Acta,* 1995, 78, 486–504) i.e., an alkoxyalkoxy group. A further preferred modification includes 2'-dimethylaminooxyethoxy, i.e., a $O(CH_2)_2ON(CH_3)_2$ group, also known as 2'-DMAOE, as described in examples hereinbelow, and 2'-dimethylaminoethoxyethoxy (also known in the art as 2'-O-dimethylaminoethoxyethyl or 2'-DMAEOE), i.e., 2 -O—$CH_2$—O—$CH_2$—N($CH_2$)$_2$, also described in examples hereinbelow.

A further prefered modification includes Locked Nucleic Acids (LNAs) in which the 2'-hydroxyl group is linked to the 3' or 4' carbon atom of the sugar ring thereby forming a bicyclic sugar moiety. The linkage is preferably a methelyne (—$CH_2$—)$_n$ group bridging the 2' oxygen atom and the 3' or 4' carbon atom wherein n is 1 or 2. LNAs and preparation thereof are described in WO 98/39352 and WO 99/14226.

Other preferred modifications include 2'-methoxy (2'-O—$CH_3$), 2'-aminopropoxy (2'-O$CH_2CH_2CH_2NH_2$), 2'-allyl (2'-$CH_2$—CH=$CH_2$), 2'-O-allyl (2'-O—$CH_2$—CH=$CH_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'–5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687, 808, those disclosed in The *Concise Encyclopedia Of Polymer Science And Engineering*, pages 858–859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, *Antisense Research and Applications*, pages 289–302, Crooke, S. T. and Lebleu, B. ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Sanghvi, Y. S., Crooke, S. T. and Lebleu, B., eds.,*Antisense Research andApplications*, CRC Press, Boca Raton, 1993, pp. 276–278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. Nos. 3,687,808, as well as U.S. Pat. Nos. 4,845,205; 5,130,302; 5,134,066; 5,175, 273; 5,367,066; 5,432,272; 5,457,187; 5,459,255; 5,484, 908; 5,502,177; 5,525,711; 5,552,540; 5,587,469; 5,594, 121, 5,596,091; 5,614,617; 5,645,985; 5,830,653; 5,763, 588; 6,005,096; and 5,681,941, certain of which are commonly owned with the instant application, and each of which is herein incorporated by reference, and U.S. Pat. No. 5,750,692, which is commonly owned with the instant application and also herein incorporated by reference.

Another modification of the oligonucleotides of the invention involves chemically linking to the oligonucleotide one or more moieties or conjugates which enhance the activity, cellular distribution or cellular uptake of the oligonucleotide. The compounds of the invention can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, lipids, phospholipids, biotin, phenazine, folate, phenanthridine, anthraquinone, acridine, fluores-ceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, filed Oct. 23, 1992 the entire disclosure of which is incorporated herein by reference. Conjugate moieties include but are not limited to lipid moieties such as a cholesterol moiety (Letsinger et al., *Proc. Natl. Acad. Sci. USA*, 1989, 86, 6553–6556), cholic acid (Manoharan et al., *Bioorg. Med. Chem. Let.*, 1994, 4, 1053–1060), a thioether, e.g., hexyl-S-tritylthiol (Manoharan et al.,*Ann. N.Y. Acad. Sci.*, 1992, 660, 306–309; Manoharan et al., *Bioorg. Med. Chem. Let.*, 1993, 3, 2765–2770), a thiocholesterol (Oberhauser et al., *Nucl. Acids Res.*, 1992, 20, 533–538), an aliphatic chain, e.g., dodecandiol or undecyl residues (Saison-Behmoaras et al., *EMBO J.*, 1991, 10, 1111–1118; Kabanov et al., *FEBS Lett.*, 1990, 259, 327–330; Svinarchuk et al., *Biochimie*, 1993, 75, 49–54), a phospholipid, e.g., di-hexadecyl-rac-glycerol or triethylammonium 1, 2-di-O-hexadecyl-rac-glycero-3-H-phosphonate (Manoharan et al., *Tetrahedron Lett.*, 1995, 36, 3651–3654; Shea et al., *Nucl. Acids Res.*, 1990, 18, 3777–3783), a polyamine or a polyethylene glycol chain (Manoharan et al., *Nucleosides & Nucleotides*, 1995, 14, 969–973), or adamantane acetic acid (Manoharan et al., *Tetrahedron Lett.*, 1995, 36, 3651–3654), a palmityl moiety (Mishra et al., *Biochim. Biophys. Acta*, 1995, 1264, 229–237), or an octadecylamine or hexylamino-carbonyl-oxycholesterol moiety (Crooke et al., *J. Pharmacol. Exp. Ther.*, 1996, 277, 923–937. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) which is incorporated herein by reference in its entirety.

Representative United States patents that teach the preparation of such oligonucleotide conjugates include, but are not limited to, U.S. Pat. Nos. 4,828,979; 4,948,882; 5,218, 105; 5,525,465; 5,541,313; 5,545,730; 5,552,538; 5,578, 717; 5,580,731; 5,580,731; 5,591,584; 5,109,124; 5,118, 802; 5,138,045; 5,414,077; 5,486,603; 5,512,439; 5,578, 718; 5,608,046; 4,587,044; 4,605,735; 4,667,025; 4,762, 779; 4,789,737; 4,824,941; 4,835,263; 4,876,335; 4,904, 582; 4,958,013; 5,082,830; 5,112,963; 5,214,136; 5,082, 830; 5,112,963; 5,214,136; 5,245,022; 5,254,469; 5,258, 506; 5,262,536; 5,272,250; 5,292,873; 5,317,098; 5,371, 241; 5,391,723; 5,416,203; 5,451,463; 5,510,475; 5,512, 667; 5,514,785; 5,565,552; 5,567,810; 5,574,142; 5,585, 481; 5,587,371; 5,595,726; 5,597,696; 5,599,923; 5,599,928 and 5,688,941, certain of which are commonly owned with the instant application, and each of which is herein incorporated by reference.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The antisense compounds of the invention are synthesized in vitro and do not include antisense compositions of biological origin, or genetic vector constructs designed to direct the in vivo synthesis of antisense molecules. The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos. 5,108,921; 5,354,844; 5,416,016; 5,459, 127; 5,521,291; 5,543,158; 5,547,932; 5,583,020; 5,591, 721; 4,426,330; 4,534,899; 5,013,556; 5,108,921; 5,213, 804; 5,227,170; 5,264,221; 5,356,633; 5,395,619; 5,416, 016; 5,417,978; 5,462,854; 5,469,854; 5,512,295; 5,527, 528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WC 93/24510 to Gosselin et al., published Dec. 9, 1993 or in WO 94/26764 and U.S. Pat. No. 5,770,713 to Imbach et al.

The term "pharmaceutically acceptable salts" refers to physiologically and pharmaceutically acceptable salts of the compounds of the invention: i.e., salts that retain the desired biological activity of the parent compound and do not impart undesired toxicological effects thereto. Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts," *J. of Pharma Sci.*, 1977, 66, 1–19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid.

Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalene-disulfonic acid, polygalacturonic acid, and the like; and (d) salts formed from elemental anions such as chlorine, bromine, and iodine.

The antisense compounds of the present invention can be utilized for diagnostics, therapeutics, prophylaxis and as research reagents and kits. For therapeutics, an animal, preferably a human, suspected of having a disease or disorder which can be treated by modulating the expression of cellular apoptosis susceptibility gene is treated by administering antisense compounds in accordance with this invention. The compounds of the invention can be utilized in pharmaceutical compositions by adding an effective amount of an antisense compound to a suitable pharmaceutically acceptable diluent or carrier. Use of the antisense compounds and methods of the invention may also be useful prophylactically, e.g., to prevent or delay infection, inflammation or tumor formation, for example.

The antisense compounds of the invention are useful for research and diagnostics, because these compounds hybridize to nucleic acids encoding cellular apoptosis susceptibility gene, enabling sandwich and other assays to easily be constructed to exploit this fact. Hybridization of the antisense oligonucleotides of the invention with a nucleic acid encoding cellular apoptosis susceptibility gene can be detected by means known in the art. Such means may include conjugation of an enzyme to the oligonucleotide, radiolabelling of the oligonucleotide or any other suitable detection means. Kits using such detection means for detecting the level of cellular apoptosis susceptibility gene in a sample may also be prepared.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Preferred topical formulations include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA). Oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters include but are not limited arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-10}$ alkyl ester (e.g. isopropylmyristate IPM), monoglyceride, diglyceride or pharmaceutically acceptable salt thereof. Topical formulations are described in detail in U.S. patent application Ser. No. 09/315,298 filed on May 20, 1999 which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Prefered bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate, sodium glycodihydrofusidate,. Prefered fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g. sodium). Also prefered are combinations of penetration enhancers, for example, fatty acids/salts in combination with bile acids/salts. A particularly prefered combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally in granular form including sprayed dried particles, or complexed to form micro or nanoparticles. Oligonucleotide complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Particularly preferred complexing agents include chitosan, N-trimethylchitosan, poly-L-lysine, polyhistidine, polyornithine, polyspermines, protamine, polyvinylpyridine, polythiodiethylamino-methylethylene P(TDAE), polyaminostyrene (e.g. p-amino), poly(methylcyanoacrylate), poly(ethylcyanoacrylate), poly(butylcyanoacrylate), poly(isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for oligonucleotides and their preparation are described in detail in U.S. applications Ser. No. 08/886,829 (filed Jul. 1, 1997), Ser. No. 09/108,673 (filed Jul. 1, 1998), Ser. No. 09/256,515 (filed Feb. 23, 1999), Ser. No. 09/082,624 (filed May 21, 1998) and Ser. No. 09/315,298 (filed May 20, 1999) each of which is incorporated herein by reference in their entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.

Emulsions

The compositions of the present invention may be prepared and formulated as emulsions. Emulsions are typically heterogenous systems of one liquid dispersed in another in the form of droplets usually exceeding 0.1 µm in diameter. (Idson, in *Pharmaceutical Dosage Forms*, Lieberman, Rieger and Banker (Eds.), 1988, Marcel Dekker, Inc., New York, N.Y., volume 1, p. 199; Rosoff, in *Pharmaceutical Dosage Forms*, Lieberman, Rieger and Banker (Eds.), 1988, Marcel Dekker, Inc., New York, N.Y., Volume 1, p. 245; Block in *Pharmaceutical Dosage Forms*, Lieberman, Rieger and Banker (Eds.), 1988, Marcel Dekker, Inc., New York, N.Y., volume 2, p. 335; Higuchi et al., in *Remington's Pharmaceutical Sciences,* Mack Publishing Co., Easton, Pa., 1985, p. 301). Emulsions are often biphasic systems comprising of two immiscible liquid phases intimately mixed and dispersed with each other. In general, emulsions may be either water-in-oil (w/o) or of the oil-in-water (o/w) variety. When an aqueous phase is finely divided into and dispersed as minute droplets into a bulk oily phase the resulting composition is called a water-in-oil (w/o) emulsion. Alternatively, when an oily phase is finely divided into and dispersed as minute droplets into a bulk aqueous phase the resulting composition is called an oil-in-water (o/w) emulsion. Emulsions may contain additional components in addition to the dispersed phases and the active drug which may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, in *Pharmaceutical Dosage Forms*, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in *Pharmaceutical Dosage Forms, Lieberman,* Rieger and Banker (Eds.), 1988, Marcel Dekker, Inc., New York, N.Y., volume 1, p. 285; Idson, in *Pharmaceutical Dosage Forms,* Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: nonionic, anionic, cationic and amphoteric (Rieger, in *Pharmaceutical Dosage Forms,* Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in *Pharmaceutical Dosage Forms,* Lieberman, Rieger and Banker (Eds.), 1988, Marcel Dekker, Inc., New York, N.Y., volume 1, p. 335; Idson, in *Pharmaceutical Dosage Forms,* Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (Idson, in *Pharmaceutical Dosage Forms,* Lieberman, Rieger and Banker (Eds.), 1988, Marcel Dekker, Inc., New York, N.Y., volume 1, p. 199). Emulsion formulations for oral delivery have been very widely used because of reasons of ease of formulation, efficacy from an absorption and bioavailability standpoint. (Rosoff, in *Pharmaceutical Dosage Forms,* Lieberman, Rieger and Banker (Eds.), 1988, Marcel Dekker, Inc., New York, N.Y., volume 1, p. 245; Idson, in *Pharmaceutical Dosage Forms,* Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment of the present invention, the compositions of oligonucleotides and nucleic acids are formulated as microemulsions. A microemulsion may be defined as a system of water, oil and amphiphile which is a single optically isotropic and thermodynamically stable liquid solution (Rosoff, in *Pharmaceutical Dosage Forms,* Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: Controlled Release of Drugs: Polymers and Aggregate Systems, Rosoff, M., Ed., 1989, VCH Publishers, New York, pages 185–215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in Remington's Pharmaceutical Sciences, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in *Pharmaceutical Dosage Forms,* Lieberman, Rieger and Banker (Eds.), 1988, Marcel Dekker, Inc., New York, N.Y., volume 1, p. 245; Block, in *Pharmaceutical Dosage Forms,* Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (S0750), decaglycerol decaoleate (DA0750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8-C12) mono, di, and tri-glycerides, polyoxyethylated glyceryl fatty acid esters, fatty alcohols, polyglycolized glycerides, saturated polyglycolized C8–C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., *Pharmaceutical Research*, 1994, 11, 1385–1390; Ritschel, Meth. Find. *Exp. Clin. Pharmacol.*, 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., *Pharmaceutical Research*, 1994, 11, 1385; Ho et al., *J. Pharm. Sci.*, 1996, 85, 138–143). Often microemulsions may form spontaneously when their components are brought together at ambient temperature. This may be particularly advantageous when formulating thermolabile drugs, peptides or oligonucleotides. Microemulsions have also been effective in the transdermal delivery of active components in both cosmetic and pharmaceutical applications. It is expected that the microemulsion compositions and formulations of the present invention will facilitate the increased systemic absorption of oligonucleotides and nucleic acids from the gastrointestinal tract, as well as improve the local cellular uptake of oligonucleotides and nucleic acids within the gastrointestinal tract, vagina, buccal cavity and other areas of administration.

Microemulsions of the present invention may also contain additional components and additives such as sorbitan monostearate (Grill 3), Labrasol, and penetration enhancers to improve the properties of the formulation and to enhance the absorption of the oligonucleotides and nucleic acids of the present invention. Penetration enhancers used in the microemulsions of the present invention may be classified as belonging to one of five broad categories—surfactants, fatty acids, bile salts, chelating agents, and non-chelating non-surfactants (Lee et al., *Critical Reviews in Therapeutic Drug Carrier Systems*, 1991, p. 92). Each of these classes has been discussed above.

Liposomes

There are many organized surfactant structures besides microemulsions that have been studied and used for the formulation of drugs. These include monolayers, micelles, bilayers and vesicles. Vesicles, such as liposomes, have attracted great interest because of their specificity and the duration of action they offer from the standpoint of drug delivery. As used in the present invention, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to cross intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include; liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in *Pharmaceutical Dosage Forms*, Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes. As the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis.

Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., *Biochem. Biophys. Res. Commun.*, 1987, 147, 980–985).

Liposomes which are pH-sensitive or negatively-charged, entrap DNA rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., *Journal of Controlled Release*, 1992, 19, 269–274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine DOPE). Another type of liposomal composition is formed from hosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g. as a solution or as an emulsion) were ineffective (Weiner et al., *Journal of Drug Targeting*, 1992, 2, 405–410). Further, an additional study tested the efficacy of interferon administered as part of a liposomal formulation to the administration of interferon using an aqueous system, and concluded that the liposomal formulation was superior to aqueous administration (du Plessis et al., *Antiviral Research*, 1992, 18, 259–265).

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et al. *S.T.P.Pharma. Sci.*, 1994, 4, 6, 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., *FEBS Letters*, 1987, 223, 42; Wu et al., *Cancer Research*, 1993, 53, 3765).

Various liposomes comprising one or more glycolipids are known in the art. Papahadjopoulos et al. (*Ann. N.Y. Acad. Sci.*, 1987, 507, 64) reported the ability of monosialoganglioside $G_{M1}$, galactocerebroside sulfate and phosphatidylinositol to improve blood half-lives of liposomes. These findings were expounded upon by Gabizon et al. (*Proc. Natl. Acad. Sci. U.S.A.*, 1988, 85, 6949). U.S. Pat. No. 4,837,028 and WO 88/04924, both to Allen et al., disclose liposomes comprising (1) sphingomyelin and (2) the ganglioside $GM_1$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al.).

Many liposomes comprising lipids derivatized with one or more hydrophilic polymers, and methods of preparation thereof, are known in the art. Sunamoto et al. (*Bull. Chem. Soc. Jpn.*, 1980, 53, 2778) described liposomes comprising a nonionic detergent, 2C1215G, that contains a PEG moiety. Illum et al. (*FEBS Lett.*, 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (*FEDS Lett.*, 1990, 268, 235) described experiments demonstrating that liposomes comprising phosphatidylethanolamine (PE) derivatized with PEG or PEG stearate have significant increases in blood circulation half-lives. Blume et al. (*Biochimica et Biophysica Acta*, 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1–20 mole percent of PE derivatized with PEG, and methods of use thereof, are described by Woodle et al. (U.S. Pat. Nos. 5,013,556 and 5,356,633) and Martin et al. (U.S. Patent No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al.). U.S. Pat. Nos. 5,540,935 (Miyazaki et al.) and 5,556,948 (Tagawa et al.) describe PEG-containing liposomes that can be further derivatized with functional moieties on their surfaces.

A limited number of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include an antisense RNA. U.S. Pat. No. 5,665,710 to Rahman et al. describes certain methods of encapsulating oligodeoxynucleotides in liposomes. WO 97/04787 to Love et al. discloses liposomes comprising antisense oligonucleotides targeted to the raf gene.

Transfersomes are yet another type of liposomes, and are highly deformable lipid aggregates which are attractive candidates for drug delivery vehicles. Transfersomes may be described as lipid droplets which are so highly deformable that they are easily able to penetrate through pores which are smaller than the droplet. Transfersomes are adaptable to the environment in which they are used, e.g. they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in *Pharmaceutical Dosage Forms,* Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in *Pharmaceutical Dosage Forms,* Marcel Dekker, Inc., New York, N.Y., 1988, p. 285).

Penetration Enhancers

In one embodiment, the present invention employs various penetration enhancers to effect the efficient delivery of nucleic acids, particularly oligonucleotides, to the skin of animals. Most drugs are present in solution in both ionized and nonionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers may be classified as belonging to one of five broad categories, i.e., surfactants, fatty acids, bile salts, chelating agents, and non-chelating non-surfactants (Lee et al., *Critical Reviews in Therapeutic Drug Carrier Systems,* 1991, p.92). Each of the above mentioned classes of penetration enhancers are described below in greater detail.

Surfactants: In connection with the present invention, surfactants (or "surface-active agents") are chemical entities which, when dissolved in an aqueous solution, reduce the surface tension of the solution or the interfacial tension between the aqueous solution and another liquid, with the result that absorption of oligonucleotides through the mucosa is enhanced. In addition to bile salts and fatty acids, these penetration enhancers include, for example, sodium lauryl sulfate, polyoxyethylene-9-lauryl ether and polyoxyethylene-20-cetyl ether) (Lee et al., *Critical Reviews in Therapeutic Drug Carrier Systems,* 1991, p.92); and perfluorochemical emulsions, such as FC-43. Takahashi et al., *J. Pharm. Pharmacol.,* 1988, 40, 252).

Fatty acids: Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-10}$ alkyl esters thereof (e.g., methyl, isopropyl and t-butyl), and mono- and di-glycerides thereof (i.e., oleate, laurate, caprate, myristate, palmitate, stearate, linoleate, etc.) (Lee et al., *Critical Reviews in Therapeutic Drug Carrier Systems,* 1991, p.92; Muranishi, *Critical Reviews in Therapeutic Drug Carrier Systems,* 1990, 7, 1–33; El Hariri et al., *J. Pharm. Pharmacol.,* 1992, 44, 651–654).

Bile salts: The physiological role of bile includes the facilitation of dispersion and absorption of lipids and fat-soluble soluble vitamins (Brunton, Chapter 38 in: Goodman & Gilman's *The Pharmacological Basis of Therapeutics,* 9th Ed., Hardman et al. Eds., McGraw-Hill, New York, 1996, pp. 934–935). Various natural bile salts, and their synthetic derivatives, act as penetration enhancers. Thus the term "bile salts" includes any of the naturally occurring components of bile as well as any of their synthetic derivatives. The bile salts of the invention include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate) taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (Lee et al., *Critical Reviews in Therapeutic Drug Carrier Systems,* 1991, page 92; Swinyard, Chapter 39 In: *Remington's Pharmaceutical Sciences,* 18th Ed., Gennaro, ed., Mack Publishing Co., Easton, Pa., 1990, pages 782–783; Muranishi, *Critical Reviews in Therapeutic Drug Carrier Systems,* 1990, 7, 1–33; Yamamoto et al., *J. Pharm. Exp. Ther.,* 1992, 263, 25; Yamashita et al., *J. Pharm. Sci.,* 1990, 79, 579–583).

Chelating Agents: Chelating agents, as used in connection with the present invention, can be defined as compounds that remove metallic ions from solution by forming complexes therewith, with the result that absorption of oligonucleotides through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, *J. Chromatogr.*, 1993, 618, 315–339). Chelating agents of the invention include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines) (Lee et al., *Critical Reviews in Therapeutic Drug Carrier Systems*, 1991, page 92; Muranishi, Critical Reviews in *Therapeutic Drug Carrier Systems*, 1990, 7, 1–33; Buur et al., *J. Control Rel.*, 1990, 14, 43–51).

Non-chelating non-surfactants: As used herein, non-chelating non-surfactant penetration enhancing compounds can be defined as compounds that demonstrate insignificant activity as chelating agents or as surfactants but that nonetheless enhance absorption of oligonucleotides through the alimentary mucosa (Muranishi, *Critical Reviews in Therapeutic Drug Carrier Systems*, 1990, 7, 1–33). This class of penetration enhancers include, for example, unsaturated cyclic ureas, 1-alkyl- and 1-alkenylazacyclo-alkanone derivatives (Lee et al., *Critical Reviews in Therapeutic Drug Carrier Systems*, 1991, page 92); and non-steroidal anti-inflammatory agents such as diclofenac sodium, indomethacin and phenylbutazone (Yamashita et al., *J. Pharm. Pharmacol.*, 1987, 39, 621–626).

Agents that enhance uptake of oligonucleotides at the cellular level may also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of oligonucleotides.

Other agents may be utilized to enhance the penetration of the administered nucleic acids, including glycols such as ethylene glycol and propylene glycol, pyrrols such as 2-pyrrol, azones, and terpenes such as limonene and menthone.

Carriers

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate oligonucleotide in hepatic tissue can be reduced when it is coadministered with polyinosinic acid, dextran sulfate, polycytidic acid or 4-acetamido-4'isothiocyano-stilbene-2,2'-disulfonic acid (Miyao et al., *Antisense Res. Dev.*, 1995, 5, 115–121; Takakura et al., *Antisense & Nucl. Acid Drug Dev.*, 1996, 6, 177–183).

Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc.).

Pharmaceutically acceptable organic or inorganic excipient suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

Other Components

The compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions may contain substances which increase the viscosity of the suspension including, for example, sodium carboxymethylcellulose, sorbitol and/or dextran. The suspension may also contain stabilizers.

Certain embodiments of the invention provide pharmaceutical compositions containing (a) one or more antisense compounds and (b) one or more other chemotherapeutic agents which function by a non-antisense mechanism. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). See, generally, *The Merck Manual of Diagnosis and Therapy,* 15th Ed. 1987, pp. 1206–1228, Berkow et al., eds., Rahway, N.J. When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to non-steroidal anti-inflammatory drugs and corticosteroids, and antiviral drugs, including but not limited to ribivirin, vidarabine, acyclovir and ganciclovir, may also be combined in compositions of the invention. See, generally, *The Merck Manual of Diagnosis and Therapy,* 15th Ed., Berkow et al., eds., 1987, Rahway, N.J., pages 2499–2506 and 46–49, respectively). Other non-antisense chemotherapeutic agents are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Numerous examples of antisense compounds are known in the art. Two or more combined compounds may be used together or sequentially.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50s}$ found to be effective in in vitro and in vivo animal models. In general, dosage is from 0.01 ug to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 100 g per kg of body weight, once or more daily, to once every 20 years.

While the present invention has been described with specificity in accordance with certain of its preferred embodiments, the following examples serve only to illustrate the invention and are not intended to limit the same.

EXAMPLES

Example 1

Nucleoside Phosphoramidites for Oligonucleotide Synthesis

Deoxy and 2'-alkoxy amidites

2'-Deoxy and 2'-methoxy beta-cyanoethyldiisopropyl phosphoramidites were purchased from commercial sources (e.g. Chemgenes, Needham Mass. or Glen Research, Inc. Sterling Va.). Other 2'-O-alkoxy substituted nucleoside amidites are prepared as described in U.S. Pat. No. 5,506, 351, herein incorporated by reference. For oligonucleotides synthesized using 2'-alkoxy amidites, the standard cycle for unmodified oligonucleotides was utilized, except the wait step after pulse delivery of tetrazole and base was increased to 360 seconds.

Oligonucleotides containing 5-methyl-2'-deoxycytidine (5-Me-C) nucleotides were synthesized according to published methods [Sanghvi, et. al., *Nucleic Acids Research,* 1993, 21, 3197–3203] using commercially available phosphoramidites (Glen Research, Sterling Va. or ChemGenes, Needham Mass.).

2'-Fluoro amidites

2'-Fluorodeoxyadenosine amidites

2'-fluoro oligonucleotides were synthesized as described previously [Kawasaki, et. al., *J. Med. Chem.,* 1993, 36, 831–841] and U.S. Pat. No. 5,670,633, herein incorporated by reference. Briefly, the protected nucleoside N6-benzoyl-2'-deoxy-2'-fluoroadenosine was synthesized utilizing commercially available 9-beta-D-arabinofuranosyladenine as starting material and by modifying literature procedures whereby the 2'-alpha-fluoro atom is introduced by a $S_N2$-displacement of a 2'-beta-trityl group. Thus N6-benzoyl-9-beta-D-arabinofuranosyladenine was selectively protected in moderate yield as the 3',5'-ditetrahydropyranyl (THP) intermediate. Deprotection of the THP and N6-benzoyl groups was accomplished using standard methodologies and standard methods were used to obtain the 5'-dimethoxytrityl-(DMT) and 5'-DMT-31-phosphoramidite intermediates.

2'-Fluorodeoxyguanosine

The synthesis of 2'-deoxy-2'-fluoroguanosine was accomplished using tetraisopropyldisiloxanyl (TPDS) protected 9-beta-D-arabinofuranosylguanine as starting material, and conversion to the intermediate diisobutyryl-arabinofuranosylguanosine. Deprotection of the TPDS group was followed by protection of the hydroxyl group with THP to give diisobutyryl di-THP protected arabinofuranosylguanine. Selective O-deacylation and triflation was followed by treatment of the crude product with fluoride, then deprotection of the THP groups. Standard methodologies were used to obtain the 5'-DMT- and 5'-DMT-3'-phosphoramidites.

2'-Fluorouridine

Synthesis of 2'-deoxy-2'-fluorouridine was accomplished by the modification of a literature procedure in which 2,2'-anhydro-1-beta-D-arabinofuranosyluracil was treated with 70% hydrogen fluoride-pyridine. Standard procedures were used to obtain the 5'-DMT and 5'-DMT-3'phosphoramidites.

2'-Fluorodeoxycytidine

2'-deoxy-2'-fluorocytidine was synthesized via amination of 2'-deoxy-2'-fluorouridine, followed by selective protection to give N4-benzoyl-2'-deoxy-2'-fluorocytidine. Standard procedures were used to obtain the 5'-DMT and 5'-DMT-3'phosphoramidites.

2'-O-(2-Methoxyethyl) modified amidites

2'-O-Methoxyethyl-substituted nucleoside amidites are prepared as follows, or alternatively, as per the methods of Martin, P., *Helvetica Chimica Acta*, 1995, 78, 486–504.

2,2'-Anhydro[1-(beta-D-arabinofuranosyl)-5-methyluridine]

5-Methyluridine (ribosylthymine, commercially available through Yamasa, Choshi, Japan) (72.0 g, 0.279 M), diphenylcarbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid that was crushed to a light tan powder (57 g, 85% crude yield). The NMR spectrum was consistent with the structure, contaminated with phenol as its sodium salt (ca. 5%). The material was used as is for further reactions (or it can be purified further by column chromatography using a gradient of methanol in ethyl acetate (10–25%) to give a white solid, mp 222–4° C.).

2'-O-Methoxyethyl-5-methyluridine 2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155–160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/acetone/MeOH (20:5:3) containing 0.5% Et3NH. The residue was dissolved in $CH_2Cl_2$ (250 mL) and adsorbed onto silica (150 g) prior to loading onto the column. The product was eluted with the packing solvent to give 160 g (63%) of product. Additional material was obtained by reworking impure fractions.

2'-O-Methoxyethyl-5'-O-dimethoxytrityl-5-methyluridine

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with $CH_3CN$ (200 mL). The residue was dissolved in $CHCl_3$ (1.5 L) and extracted with 2×500 mL of saturated $NaHCO_3$ and 2×500 mL of saturated NaCl. The organic phase was dried over $Na_2SO_4$, filtered and evaporated. 275 g of residue was obtained. The residue was purified on a 3.5 kg silica gel column, packed and eluted with EtOAc/hexane/acetone (5:5:1) containing 0.5% $Et_3NH$. The pure fractions were evaporated to give 164 g of product. Approximately 20 g additional was obtained from the impure fractions to give a total yield of 183 g (57%).

3'-O-Acetyl-2'-O-methoxyethyl-5'-O-dimethoxytrityl-5-methyluridine

2'-O-Methoxyethyl-5'-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by TLC by first quenching the TLC sample with the addition of MeOH. Upon completion of the reaction, as judged by TLC, MeOH (50 mL) was added and the mixture evaporated at 35° C. The residue was dissolved in $CHCl_3$ (800 mL) and extracted with 2×200 mL of saturated sodium bicarbonate and 2×200 mL of saturated NaCl. The water layers were back extracted with 200 mL of $CHCl_3$. The combined organics were dried with sodium sulfate and evaporated to give 122 g of residue (approx. 90% product). The residue was purified on a 3.5 kg silica gel column and eluted using EtOAc/hexane(4:1). Pure product fractions were evaporated to yield 96 g (84%). An additional 1.5 g was recovered from later fractions.

3'-O-Acetyl-2'-O-methoxyethyl-5'-O-dimethoxytrityl-5-methyl-4-triazoleuridine

A first solution was prepared by dissolving 3'-O-acetyl-2'-O-methoxyethyl-5'-O-dimethoxytrityl-5-methyluridine (96 g, 0.144 M) in $CH_3CN$ (700 mL) and set aside. Triethylamine (189 mL, 1.44 M) was added to a solution of triazole (90 g, 1.3 M) in $CH_3CN$ (1 L), cooled to −5° C. and stirred for 0.5 h using an overhead stirrer. $POCl_3$ was added dropwise, over a 30 minute period, to the stirred solution maintained at 0–10° C., and the resulting mixture stirred for an additional 2 hours. The first solution was added dropwise, over a 45 minute period, to the latter solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of $NaHCO_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methylcytidine

A solution of 3'-O-acetyl-2'-O-methoxyethyl-5'-O-dimethoxytrityl-5-methyl-4-triazoleuridine (103 g, 0.141 M) in dioxane (500 mL) and $NH_4OH$ (30 mL) was stirred at-room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with $NH_3$ gas was added and the vessel heated to 100° C. for 2 hours (TLC showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

N4-Benzoyl-2'-O-methoxyethyl-5'-O-dimethoxytrityl-5-methylcytidine

2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, TLC showed the reaction to be approximately 95% complete. The solvent was evaporated and the residue azeotroped with MeOH (200 mL). The residue was dissolved in CHCl₃ (700 mL) and extracted with saturated NaHCO₃ (2×300 mL) and saturated NaCl (2×300 mL), dried over MgSO₄ and evaporated to give a residue (96 g). The residue was chromatographed on a 1.5 kg silica column using EtOAc/hexane (1:1) containing 0.5% Et₃NH as the eluting solvent. The pure product fractions were evaporated to give 90 g (90%) of the title compound.

N4-Benzoyl-2'-O-methoxyethyl-5'-O-dimethoxytrityl-5-methylcytidine-3'-amidite

N4-Benzoyl-2'-O-methoxyethyl-5'-O-dimethoxytrityl-5-methylcytidine (74 g, 0.10 M) was dissolved in CH₂Cl₂ (1 L) Tetrazole diisopropylamine (7.1 g) and 2-cyanoethoxy-tetra-(isopropyl)phosphite (40.5 mL, 0.123 M) were added with stirring, under a nitrogen atmosphere. The resulting mixture was stirred for 20 hours at room temperature (TLC showed the reaction to be 95% complete). The reaction mixture was extracted with saturated NaHCO₃ (1×300 mL) and saturated NaCl (3×300 mL). The aqueous washes were back-extracted with CH₂Cl₂ (300 mL), and the extracts were combined, dried over MgSO₄ and concentrated. The residue obtained was chromatographed on a 1.5 kg silica column using EtOAc/hexane (3:1) as the eluting solvent. The pure fractions were combined to give 90.6 g (87%) of the title compound.

2'-O-(Aminooxyethyl) nucleoside amidites and 2'-O-(dimethylaminooxyethyl) nucleoside amidites 2'-(Dimethylaminooxyethoxy) nucleoside amidites 2'-(Dimethylaminooxyethoxy) nucleoside amidites [also known in the art as 2'-O-(dimethylaminooxyethyl) nucleoside amidites] are prepared as described in the following paragraphs. Adenosine, cytidine and guanosine nucleoside amidites are prepared similarly to the thymidine (5-methyluridine) except the exocyclic amines are protected with a benzoyl moiety in the case of adenosine and cytidine and with isobutyryl in the case of guanosine.

5'-O-tert-Butyldiphenylsilyl-O²-2'-anhydro-5-methyluridine

O²-2'-anhydro-5-methyluridine (Pro. Bio. Sint., Varese, Italy, 100.0 g, 0.416 mmol), dimethylaminopyridine (0.66 g, 0.013 eq, 0.0054 mmol) were dissolved in dry pyridine (500 ml) at ambient temperature under an argon atmosphere and with mechanical stirring. tert-Butyldiphenylchlorosilane (125.8 g, 119.0 mL, 1.1 eq, 0.458 mmol) was added in one portion. The reaction was stirred for 16 h at ambient temperature. TLC (Rf 0.22, ethyl acetate) indicated a complete reaction. The solution was concentrated under reduced pressure to a thick oil. This was partitioned between dichloromethane (1 L) and saturated sodium bicarbonate (2×1 L) and brine (1 L). The organic layer was dried over sodium sulfate and concentrated under reduced pressure to a thick oil. The oil was dissolved in a 1:1 mixture of ethyl acetate and ethyl ether (600 mL) and the solution was cooled to −10° C. The resulting crystalline product was collected by filtration, washed with ethyl ether (3×200 mL) and dried (40° C., 1 mm Hg, 24 h) to 149 g (74.8%) of white solid. TLC and NMR were consistent with pure product.

5'-O-tert-Butyldiphenylsilyl-2'-O-(2-hydroxyethyl)-5-methyluridine

In a 2 L stainless steel, unstirred pressure reactor was added borane in tetrahydrofuran (1.0 M, 2.0 eq, 622 mL). In the fume hood and with manual stirring, ethylene glycol (350 mL, excess) was added cautiously at first until the evolution of hydrogen gas subsided. 5'-O-tert-Butyldiphenylsilyl-O²-2'-anhydro-5-methyluridine (149 g, 0.311 mol) and sodium bicarbonate (0.074 g, 0.003 eq) were added with manual stirring. The reactor was sealed and heated in an oil bath until an internal temperature of 160° C. was reached and then maintained for 16 h (pressure<100 psig). The reaction vessel was cooled to ambient and opened. TLC (Rf 0.67 for desired product and Rf 0.82 for ara-T side product, ethyl acetate) indicated about 70% conversion to the product. In order to avoid additional side product formation, the reaction was stopped, concentrated under reduced pressure (10 to 1 mm Hg) in a warm water bath (40–100° C.) with the more extreme conditions used to remove the ethylene glycol. [Alternatively, once the low boiling solvent is gone, the remaining solution can be partitioned between ethyl acetate and water. The product will be in the organic phase.] The residue was purified by column chromatography (2 kg silica gel, ethyl acetate-hexanes gradient 1:1 to 4:1). The appropriate fractions were combined, stripped and dried to product as a white crisp foam (84 g, 50%), contaminated starting material (17.4 g) and pure reusable starting material 20 g. The yield based on starting material less pure recovered starting material was 58%. TLC and NMR were consistent with 99% pure product.

2'-O-([2-phthalimidoxy)ethyl]-5'-t-butyldiphenylsilyl-5-methyluridine

5'-tert-Butyldiphenylsilyl-2'-O-(2-hydroxyethyl)-5-methyluridine (20 g, 36.98 mmol) was mixed with triphenylphosphine (11.63 g, 44.36 mmol) and N-hydroxyphthalimide (7.24 g, 44.36 mmol). It was then dried over P₂O₅ under high vacuum for two days at 40° C. The reaction mixture was flushed with argon and dry THF (369.8 mL, Aldrich, sure seal bottle) was added to get a clear solution. Diethyl-azodicarboxylate (6.98 mL, 44.36 mmol) was added dropwise to the reaction mixture. The rate of addition is maintained such that resulting deep red coloration is just discharged before adding the next drop. After the addition was complete, the reaction was stirred for 4 hrs. By that time TLC showed the completion of the reaction (ethylacetate:hexane, 60:40). The solvent was evaporated in vacuum. Residue obtained was placed on a flash column and eluted with ethyl acetate:hexane (60:40), to get 2'-O-([2-phthalimidoxy)ethyl]-5'-t-butyldiphenylsilyl-5-methyluridine as white foam (21.819 g, 86%).

5'-O-tert-butyldiphenylsilyl-2'-O-[(2-formadoximinooxy)ethyl]-5-methyluridine

2'-O-([2-phthalimidoxy)ethyl]-5'-t-butyldiphenylsilyl-5-methyluridine (3.1 g, 4.5 mmol) was dissolved in dry CH₂Cl₂ (4.5 mL) and methylhydrazine (300 mL, 4.64 mmol) was added dropwise at −10° C. to 0° C. After 1 h the mixture was filtered, the filtrate was washed with ice cold CH₂Cl₂ and the combined organic phase was washed with water, brine and dried over anhydrous Na₂SO₄. The solution was concentrated to get 2'-O-(aminooxyethyl) thymidine, which was then dissolved in MeOH (67.5 mL). To this formaldehyde (20% aqueous solution, w/w, 1.1 eq.) was added and the resulting mixture was stirred for 1 h. Solvent was removed under vacuum; residue chromatographed to get 5'-O-tert-butyldiphenylsilyl-2'-O-[(2-formadoximinooxy) ethyl]-5-methyluridine as white foam (1.95 g, 78%).

5'-O-tert-Butyldiphenylsilyl-2'-O-[N,N-dimethylaminooxyethyl]-5-methyluridine

5'-O-tert-butyldiphenylsilyl-2'-O-[(2-formadoximinooxy) ethyl]-5-methyluridine (1.77 g, 3.12 mmol) was dissolved in a solution of 1M pyridinium p-toluenesulfonate (PPTS) in dry MeOH (30.6 mL). Sodium cyanoborohydride (0.39 g, 6.13 mmol) was added to this solution at 10° C. under inert atmosphere. The reaction mixture was stirred for 10 minutes at 10° C. After that the reaction vessel was removed from the ice bath and stirred at room temperature for 2 h, the reaction monitored by TLC (5% MeOH in CH$_2$Cl$_2$). Aqueous NaHCO3 solution (5%, 10 mL) was added and extracted with ethyl Adacetate (2×20 mL). Ethyl acetate phase was dried over anhydrous Na$_2$SO$_4$, evaporated to dryness. Residue was dissolved in a solution of 1M PPTS in MeOH (30.6 mL). Formaldehyde (20% w/w, 30 mL, 3.37 mmol) was added and the reaction mixture was stirred at room temperature for 10 minutes. Reaction mixture cooled to 10° C. in an ice bath, sodium cyanoborohydride (0.39 g, 6.13 mmol) was added and reaction mixture stirred at 10° C. for 10 minutes. After 10 minutes, the reaction mixture was removed from the ice bath and stirred at room temperature for 2 hrs. To the reaction mixture 5% NaHCO3 (25 mL) solution was added and extracted with ethyl acetate (2×25 mL). Ethyl acetate layer was dried over anhydrous Na$_2$SO$_4$ and evaporated to dryness. The residue obtained was purified by flash column chromatography and eluted with 5% MeOH in CH$_2$Cl$_2$ to get 5'-O-tert-butyldiphenylsilyl-2'-O-[N,N-dimethylaminooxyethyl]-5-methyluridine as a white foam (14.6 g, 80%).

2'-O-(dimethylaminooxyethyl)-5-methyluridine

Triethylamine trihydrofluoride (3.91 mL, 24.0 mmol) was dissolved in dry THF and triethylamine (1.67 mL, 12 mmol, dry, kept over KOH). This mixture of triethylamine-2HF was then added to 5'-O-tert-butyldiphenylsilyl-2'-O-[N,N-dimethylaminooxyethyl]-5-methyluridine (1.40 g, 2.4 mmol) and stirred at room temperature for 24 hrs. Reaction was monitored by TLC (5% MeOH in CH$_2$Cl$_2$). Solvent was removed under vacuum and the residue placed on a flash column and eluted with 10% MeOH in CH$_2$Cl$_2$ to get 2'-O-(dimethylaminooxyethyl)-5-methyluridine (766 mg, 92.5%).

5'-O-DMT-2'-O-(dimethylaminooxyethyl)-5-methyluridine

2'-O-(dimethylaminooxyethyl)-5-methyluridine (750 mg, 2.17 mmol) was dried over P$_2$O$_5$ under high vacuum overnight at 40° C. It was then co-evaporated with anhydrous pyridine (20 mL). The residue obtained was dissolved in pyridine (11 mL) under argon atmosphere. 4-dimethylaminopyridine (26.5 mg, 2.60 mmol), 4,4'-dimethoxytrityl chloride (880 mg, 2.60 mmol) was added to the mixture and the reaction mixture was stirred at room temperature until all of the starting material disappeared. Pyridine was removed under vacuum and the residue chromatographed and eluted with 10% MeOH in CH$_2$Cl$_2$ (containing a few drops of pyridine) to get 5'-O-DMT-2'-O-(dimethylamino-oxyethyl)-5-methyluridine (1.13 g, 80%).

5'-O-DMT-2'-O-(2-N,N-dimethylaminooxyethyl)-5-methyluridine-3'-[(2-cyanoethyl)-N,N-diisopropylphosphoramidite]

5'-O-DMT-2'-O-(dimethylaminooxyethyl)-5-methyluridine (1.08 g, 1.67 mmol) was co-evaporated with toluene (20 mL). To the residue N,N-diisopropylamine tetrazonide (0.29 g, 1.67 mmol) was added and dried over P$_2$O$_5$ under high vacuum overnight at 40° C. Then the reaction mixture was dissolved in anhydrous acetonitrile (8.4 mL) and 2-cyanoethyl-N,N,N$^1$,N$^1$-tetraisopropylphosphoramidite (2.12 mL, 6.08 mmol) was added. The reaction mixture was stirred at ambient temperature for 4 hrs under inert atmosphere. The progress of the reaction was monitored by TLC (hexane:ethyl acetate 1:1). The solvent was evaporated, then the residue was dissolved in ethyl acetate (70 mL) and washed with 5% aqueous NaHCO$_3$ (40 mL). Ethyl acetate layer was dried over anhydrous Na$_2$SO$_4$ and concentrated. Residue obtained was chromatographed (ethyl acetate as eluent) to get 5'-O-DMT-2'-O-(2-N,N-dimethylaminooxyethyl)-5-methyluridine-3'-[(2-cyanoethyl)-N,N-diisopropylphosphoramidite] as a foam (1.04 g, 74.9%).

2'-(Aminooxyethoxy) nucleoside amidites

2'-(Aminooxyethoxy) nucleoside amidites [also known in the art as 2'-O-(aminooxyethyl) nucleoside amidites] are prepared as described in the following paragraphs. Adenosine, cytidine and thymidine nucleoside amidites are prepared similarly.

N2-isobutyryl-6-O-diphenylcarbamoyl-2'-O-(2-ethylacetyl)-5N-O-(4,4'-dimethoxytrityl)guanosine-3'-[(2-cyanoethyl)-N,N-diisopropylphosphoramidite]

The 2'-O-aminooxyethyl guanosine analog may be obtained by selective 2'-O-alkylation of diaminopurine riboside. Multigram quantities of diaminopurine riboside may be purchased from Schering AG (Berlin) to provide 2'-O-(2-ethylacetyl) diaminopurine riboside along with a minor amount of the 3'-O-isomer. 2'-O-(2-ethylacetyl) diaminopurine riboside may be resolved and converted to 2'-O-(2-ethylacetyl)guanosine by treatment with adenosine deaminase. (McGee, D. P. C., Cook, P. D., Guinosso, C. J., WO 94/02501 A1 940203.) Standard protection procedures should afford 2'-O-(2-ethylacetyl)-5'-O-(4,4'-dimethoxytrityl)guanosine and 2-N-isobutyryl-6-O-diphenylcarbamoyl-2'-O-(2-ethylacetyl)-5'-O-(4,4'-dimethoxytrityl)guanosine which may be reduced to provide 2-N-isobutyryl-6-O-diphenylcarbamoyl-2'-O-(2-ethylacetyl)-5'-O-(4,4'-dimethoxytrityl)guanosine. As before the hydroxyl group may be displaced by N-hydroxyphthalimide via a Mitsunobu reaction, and the protected nucleoside may phosphitylated as usual to yield 2-N-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite].

2'-dimethylaminoethoxyethoxy (2'-DMAEOE) nucleoside amidites

2'-dimethylaminoethoxyethoxy nucleoside amidites (also known in the art as 2'-O-dimethylaminoethoxyethyl, i.e., 2'-O—CH$_2$—O—CH$_2$—N(CH$_2$)$_2$, or 2'-DMAEOE nucleoside amidites) are prepared as follows. Other nucleoside amidites are prepared similarly.

2'-O-[2(2-N,N-dimethylaminoethoxy)ethyl]-5-methylethyl uridine

2[2-(Dimethylamino)ethoxy]ethanol (Aldrich, 6.66 g, 50 mmol) is slowly added to a solution of borane in tetrahydrofuran (1 M, 10 mL, 10 mmol) with stirring in a 100 mL bomb. Hydrogen gas evolves as the solid dissolves. O$^2$-,2'-anhydro-5-methyluridine (1.2 g, 5 mmol), and sodium bicarbonate (2.5 mg) are added and the bomb is sealed, placed in an oil bath and heated to 155° C. for 26 hours. The bomb is cooled to room temperature and opened. The crude solution is concentrated and the residue partitioned between water (200 mL) and hexanes (200 mL). The excess phenol is extracted into the hexane layer. The aqueous layer is extracted with ethyl acetate (3×200 mL) and the combined organic layers are washed once with water, dried over anhydrous sodium sulfate and concentrated. The residue is columned on silica gel using methanol/methylene chloride 1:20 (which has 2% triethylamine) as the eluent. As the column fractions are concentrated a colorless solid forms which is collected to give the title compound as a white solid.

5'-O-dimethoxytrityl-2'-O-[2(2-N,N-dimethylaminoethoxy)ethyl)]-5-methyl uridine

To 0.5 g (1.3 mmol) of 2'-O-[2(2-N,N-dimethylaminoethoxy)ethyl)]-5-methyl uridine in anhydrous pyridine (8 mL), triethylamine (0.36 mL) and dimethoxytrityl chloride (DMT-Cl, 0.87 g, 2 eq.) are added and stirred for 1 hour. The reaction mixture is poured into water (200 mL) and extracted with $CH_2Cl_2$ (2×200 mL). The combined $CH_2Cl_2$ layers are washed ith saturated $NaHCO_3$ solution, followed by saturated NaCl solution and dried over anhydrous sodium sulfate. Evaporation of the solvent followed by silica gel chromatography using MeOH:$CH_2Cl_2$:$Et_3N$ (20:1, v/v, with 1% triethylamine) gives the title compound.

5'-O-Dimethoxytrityl-2'-O-[2(2-N,N-dimethylaminoethoxy)-ethyl)]-5-methyl uridine-3'-O-(cyanoethyl-N,N-diisopropyl)phosphoramidite Diisopropylaminotetrazolide (0.6 g) and 2-cyanoethoxy-N,N-diisopropyl phosphoramidite (1.1 mL, 2 eq.) are added to a solution of 5'-O-dimethoxytrityl-2'-O-[2(2-N,N-dimethylaminoethoxy)ethyl)]-5-methyluridine (2.17 g, 3 mmol) dissolved in $CH_2Cl_2$ (20 mL) under an atmosphere of argon. The reaction mixture is stirred overnight and the solvent evaporated. The resulting residue is purified by silica gel flash column chromatography with ethyl acetate as the eluent to give the title compound.

Example 2

Oligonucleotide Synthesis

Unsubstituted and substituted phosphodiester (P=O) oligonucleotides are synthesized on an automated DNA synthesizer (Applied Biosystems model 380B) using standard phosphoramidite chemistry with oxidation by iodine.

Phosphorothioates (P=S) are synthesized as for the phosphodiester oligonucleotides except the standard oxidation bottle was replaced by 0.2 M solution of 3H-1,2-benzodithiole-3-one 1,1-dioxide in acetonitrile for the stepwise thiation of the phosphite linkages. The thiation wait step was increased to 68 sec and was followed by the capping step. After cleavage from the CPG column and deblocking in concentrated ammonium hydroxide at 55° C. (18 h), the oligonucleotides were purified by precipitating twice with 2.5 volumes of ethanol from a 0.5 M NaCl solution.

Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. Nos. 5,610,289 or 5,625,050, herein incorporated by reference.

Phosphoramidite oligonucleotides are prepared as described in U.S. Pat. Nos. 5,256,775 or 5,366,878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Example 3

Oligonucleoside Synthesis

Methylenemethylimino linked oligonucleosides, also identified as MMI linked oligonucleosides, methylenedimethyl-hydrazo linked oligonucleosides, also identified as MDH linked oligonucleosides, and methylenecarbonylamino linked oligonucleosides, also identified as amide-3 linked oligonucleosides, and methyleneaminocarbonyl linked oligo-nucleosides, also identified as amide-4 linked oligonucleo-sides, as well as mixed backbone compounds having, for instance, alternating MMI and P=O or P=S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 4

PNA Synthesis

Peptide nucleic acids (PNAs) are prepared in accordance with any of the various procedures referred to in Peptide Nucleic Acids (PNA): Synthesis, Properties and Potential Applications, *Bioorganic & Medicinal Chemistry*, 1996, 4, 5–23. They may also be prepared in accordance with U.S. Pat. Nos. 5,539,082, 5,700,922, and 5,719,262, herein incorporated by reference.

Example 5

Synthesis of Chimeric Oligonucleotides

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2'-O-Me]—[2'-deoxy]—[2'-O-Me] Chimeric Phosphorothioate Oligonucleotides

Chimeric oligonucleotides having 2'-O-alkyl phosphorothioate and 2'-deoxy phosphorothioate oligo-nucleotide segments are synthesized using an Applied Biosystems automated DNA synthesizer Model 380B, as above. Oligonucleotides are synthesized using the automated synthesizer and 2'-deoxy-5'-dimethoxytrityl-3'-O-phosphor-amidite for the DNA portion and 5'-dimethoxytrityl-2'-O-methyl-3'-O-phosphoramidite for 5' and 3' wings. The standard synthesis cycle is modified by increasing the wait step after the delivery of tetrazole and base to 600 s repeated four times for RNA and twice for 2'-O-methyl. The fully protected oligonucleotide is cleaved from the support and the phosphate group is deprotected in 3:1 ammonia/ethanol at room temperature overnight then lyophilized to dryness. Treatment in methanolic ammonia for 24 hrs at room temperature is then done to deprotect all bases and sample was again lyophilized to dryness. The pellet is resuspended in 1M TBAF in THF for 24 hrs at room temperature to deprotect the 2' positions. The reaction is then quenched with 1M TEAA and the sample is then reduced to 1/2 volume by rotovac before being desalted on a G25 size exclusion column. The oligo recovered is then analyzed spectrophotometrically for yield and for purity by capillary electrophoresis and by mass spectrometry.

[2'-O-(2-Methoxyethyl)]—[2'-deoxy]—[2'-O-(Methoxyethyl)] Chimeric Phosphorothioate Oligonucleotides

[2'-O-(2-methoxyethyl)]—[2'-deoxy]—[-2'-O-(methoxyethyl)] chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

[2'-O-(2-Methoxyethyl)Phosphodiester]—[2'-deoxy Phosphorothioate]—[2'-O-(2-Methoxyethyl) Phosphodiester] Chimeric Oligonucleotides

[2'-O-(2-methoxyethyl phosphodiester]—[2'-deoxy phosphorothioate]—[2'-O-(methoxyethyl) phosphodiester] chimeric oligonucleotides are prepared as per the above procedure for the 2'-O-methyl chimeric oligonucleotide with the substitution of 2'-O-(methoxyethyl) amidites for the 2'-O-methyl amidites, oxidization with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 6

Oligonucleotide Isolation

After cleavage from the controlled pore glass column (Applied Biosystems) and deblocking in concentrated ammonium hydroxide at 55° C. for 18 hours, the oligonucleotides or oligonucleosides are purified by precipitation twice out of 0.5 M NaCl with 2.5 volumes ethanol. Synthesized oligonucleotides were analyzed by polyacrylamide gel electrophoresis on denaturing gels and judged to be at least 85% full length material. The relative amounts of phosphorothioate and phosphodiester linkages obtained in synthesis were periodically checked by $^{31}P$ nuclear magnetic resonance spectroscopy, and for some studies oligonucleotides were purified by HPLC, as described by Chiang et al., *J. Biol. Chem.* 1991, 266, 18162–18171. Results obtained with HPLC-purified material were similar to those obtained with non-HPLC purified material.

Example 7

Oligonucleotide Synthesis—96 Well Plate Format

Oligonucleotides were synthesized via solid phase P(III) phosphoramidite chemistry on an automated synthesizer capable of assembling 96 sequences simultaneously in a standard 96 well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyldiisopropyl phosphoramidites were purchased from commercial vendors (e.g. PE-Applied Biosystems, Foster City, Calif., or Pharmacia, Piscataway, N.J.). Non-standard nucleosides are synthesized as per known literature or patented methods. They are utilized as base protected beta-cyanoethyldiisopropyl phosphoramidites.

Oligonucleotides were cleaved from support and deprotected with concentrated $NH_4OH$ at elevated temperature (55–60° C.) for 12–16 hours and the released product then dried in vacuo. The dried product was then re-suspended in sterile water to afford a master plate from which all analytical and test plate samples are then diluted utilizing robotic pipettors.

Example 8

Oligonucleotide Analysis—96 Well Plate Format

The concentration of oligonucleotide in each well was assessed by dilution of samples and UV absorption spectroscopy. The full-length integrity of the individual products was evaluated by capillary electrophoresis (CE) in either the 96 well format (Beckman P/ACE™ MDQ) or, for individually prepared samples, on a commercial CE apparatus (e.g., Beckman P/ACE™ 5000, ABI 270). Base and backbone composition was confirmed by mass analysis of the compounds utilizing electrospray-mass spectroscopy. All assay test plates were diluted from the master plate using single and multi-channel robotic pipettors. Plates were judged to be acceptable if at least 85% of the compounds on the plate were at least 85% full length.

Example 9

Cell Culture and Oligonucleotide Treatment

The effect of antisense compounds on target nucleic acid expression can be tested in any of a variety of cell types provided that the target nucleic acid is present at measurable levels. This can be routinely determined using, for example, PCR or Northern blot analysis. The following 4 cell types are provided for illustrative purposes, but other cell types can be routinely used, provided that the target is expressed in the cell type chosen. This can be readily determined by methods routine in the art, for example Northern blot analysis, Ribonuclease protection assays, or RT-PCR.

T-24 Cells

The human transitional cell bladder carcinoma cell line HT-24 was obtained from the American Type Culture Collection (ATCC) (Manassas, Va.). T-24 cells were routinely cultured in complete McCoy's 5A basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells were routinely passaged by trypsinization and dilution when they reached 90% confluence. Cells were seeded into 96-well plates (Falcon-Primaria #3872) at a density of 7000 cells/well for use in RT-PCR analysis.

For Northern blotting or other analysis, cells may be seeded onto 100 mm or other standard tissue culture plates and treated similarly, using appropriate volumes of medium and oligonucleotide.

A549 Cells

The human lung carcinoma cell line A549 was obtained from the American Type Culture Collection (ATCC) (Manassas, Va.). A549 cells were routinely cultured in DMEM basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells were routinely passaged by trypsinization and dilution when they reached 90% confluence.

NHDF Cells

Human neonatal dermal fibroblast (NHDF) were obtained from the Clonetics Corporation (Walkersville Md.). NHDFs were routinely maintained in Fibroblast Growth Medium (Clonetics Corporation, Walkersville Md.) supplemented as recommended by the supplier. Cells were maintained for up to 10 passages as recommended by the supplier.

HEK Cells

Human embryonic keratinocytes (HEK) were obtained from the Clonetics Corporation (Walkersville Md.). HEKs were routinely maintained in Keratinocyte Growth Medium (Clonetics Corporation, Walkersville Md.) formulated as recommended by the supplier. Cells were routinely maintained for up to 10 passages as recommended by the supplier.

Treatment with Antisense Compounds

When cells reached 80% confluency, they were treated with oligonucleotide. For cells grown in 96-well plates, wells were washed once with 200 µL OPTI-MEM™-1 reduced-serum medium (Gibco BRL) and then treated with 130 lL of OPTI-MEM™-1 containing 3.75 µg/mL LIPOFECTIN™ (Gibco BRL) and the desired concentration of oligonucleotide. After 4–7 hours of treatment, the medium was replaced with fresh medium. Cells were harvested 16–24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is ISIS 13920, TCCGTCATCGCTCCTCAGGG, SEQ ID NO: 1, a 2'-O-methoxyethyl gapmer (2'-O-methoxyethyls shown in bold) with a phosphorothioate backbone which is targeted to human H-ras. For mouse or rat cells the positive control oligonucleotide is ISIS 15770, ATGCATTCTGCCCCCAAGGA, SEQ ID NO: 2, a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-Ha-ras (for ISIS 13920) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of H-ras or c-raf mRNA is then utilized as the oligonucleotide screening concentration in subsequent experiments for that cell line. If 60% inhibition is not achieved, that particular cell line is deemed as unsuitable for oligonucleotide transfection experiments.

Example 10

Analysis of Oligonucleotide Inhibition of Cellular Apoptosis Susceptibility Gene Expression Antisense modulation of cellular apoptosis susceptibility gene expression can be assayed in a variety of ways known in the art. For example, cellular apoptosis susceptibility gene mRNA levels can be quantitated by, e.g., Northern blot analysis, competitive polymerase chain reaction (PCR), or real-time PCR (RT-PCR). Real-time quantitative PCR is presently preferred. RNA analysis can be performed on total cellular RNA or poly(A)+mRNA. Methods of RNA isolation are taught in, for example, Ausubel, F. M. et al., Current Protocols in Molecular Biology, Volume 1, pp. 4.1.1–4.2.9 and 4.5.1–4.5.3, John Wiley & Sons, Inc., 1993. Northern blot analysis is routine in the art and is taught in, for example, Ausubel, F. M. et al., Current Protocols in Molecular Biology, Volume 1, pp. 4.2.1–4.2.9, John Wiley & Sons, Inc., 1996. Real-time quantitative (PCR) can be conveniently accomplished using the commercially available ABI PRISM™ 7700 Sequence Detection System, available from PE-Applied Biosystems, Foster City, Calif. and used according to manufacturer's instructions.

Protein levels of cellular apoptosis susceptibility gene can be quantitated in a variety of ways well known in the art, such as immunoprecipitation, Western blot analysis (immunoblotting), ELISA or fluorescence-activated cell sorting (FACS). Antibodies directed to cellular apoptosis susceptibility gene can be identified and obtained from a variety of sources, such as the MSRS catalog of antibodies (Aerie Corporation, Birmingham, Mich.), or can be prepared via conventional antibody generation methods. Methods for preparation of polyclonal antisera are taught in, for example, Ausubel, F. M. et al., Current Protocols in Molecular Biology, Volume 2, pp. 11.12.1–11.12.9, John Wiley & Sons, Inc., 1997. Preparation of monoclonal antibodies is taught in, for example, Ausubel, F. M. et al., Current Protocols in Molecular Biology, Volume 2, pp. 11.4.1–11.11.5, John Wiley & Sons, Inc., 1997.

Immunoprecipitation methods are standard in the art and can be found at, for example, Ausubel, F. M. et al., Current Protocols in Molecular Biology, Volume 2, pp. 10.16.1–10.16.11, John Wiley & Sons, Inc., 1998. Western blot (immunoblot) analysis is standard in the art and can be found at, for example, Ausubel, F. M. et al., Current Protocols in Molecular Biology, Volume 2, pp. 10.8.1–10.8.21, John Wiley & Sons, Inc., 1997. Enzyme-linked immunosorbent assays (ELISA) are standard in the art and can be found at, for example, Ausubel, F. M. et al., Current Protocols in Molecular Biology, Volume 2, pp. 11.2.1–11.2.22, John Wiley & Sons, Inc., 1991.

Example 11

Poly(A)+mRNA Isolation

Poly(A)+mRNA was isolated according to Miura et al., Clin. Chem., 1996, 42, 1758–1764. Other methods for poly(A)+mRNA isolation are taught in, for example, Ausubel, F. M. et al., Current Protocols in Molecular Biology, Volume 1, pp. 4.5.1–4.5.3, John Wiley & Sons, Inc., 1993. Briefly, for cells grown on 96-well plates, growth medium was removed from the cells and each well was washed with 200 µL cold PBS. 60 µL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 µL of lysate was transferred to Oligo d(T) coated 96-well plates (AGCT Inc., Irvine Calif.). Plates were incubated for 60 minutes at room temperature, washed 3 times with 200 µL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 µL of elution buffer (5 mM Tris-HCl pH 7.6), preheated to 70° C. was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Example 12

Total RNA Isolation

Total RNA was isolated using an RNEASY 96™ kit and buffers purchased from Qiagen Inc. (Valencia Calif.) following the manufacturer's recommended procedures. Briefly, for cells grown on 96-well plates, growth medium was removed from the cells and each well was washed with 200 µL cold PBS. 100 µL Buffer RLT was added to each well and the plate vigorously agitated for 20 seconds. 100 µL of 70% ethanol was then added to each well and the contents mixed by pipetting three times up and down. The samples were then transferred to the RNEASY 96™ well plate attached to a QIAVAC™ manifold fitted with a waste collection tray and attached to a vacuum source. Vacuum was applied for 15 seconds. 1 mL of Buffer RW1 was added to each well of the RNEASY 96™ plate and the vacuum again applied for 15 seconds. 1 mL of Buffer RPE was then added to each well of the RNEASY 96™ plate and the vacuum applied for a period of 15 seconds. The Buffer RPE wash was then repeated and the vacuum was applied for an additional 10 minutes. The plate was then removed from the QIAVAC™ manifold and blotted dry on paper towels. The plate was then re-attached to the QIAVAC™ manifold fitted with a collection tube rack containing 1.2 mL collection tubes. RNA was then eluted by pipetting 60 µL water into each well, incubating 1 minute, and then applying the vacuum for 30 seconds. The elution step was repeated with an additional 60 µL water.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 13

Real-time Quantitative PCR Analysis of Cellular Apoptosis Susceptibility Gene mRNA Levels Quantitation of cellular apoptosis susceptibility gene mRNA levels was determined by real-time quantitative PCR using the ABI PRISM™ 7700 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR, in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., JOE, FAM, or VIC, obtained from either Operon Technologies Inc., Alameda, Calif. or PE-Applied Biosystems, Foster City, Calif.) is attached to the 5' end of the probe and a quencher dye (e.g., TAMRA, obtained from either Operon Technologies Inc., Alameda, Calif. or PE-Applied Biosystems, Foster City, Calif.) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ 7700 Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

PCR reagents were obtained from PE-Applied Biosystems, Foster City, Calif. RT-PCR reactions were carried out by adding 25 µL PCR cocktail (1×TAQMAN™ buffer A, 5.5 mM $MgCl_2$, 300 µM each of DATP, dCTP and dGTP, 600 µM of dUTP, 100 nM each of forward primer, reverse primer, and probe, 20 Units RNAse inhibitor, 1.25 Units AMPLITAQ GOLD™, and 12.5 Units MuLV reverse transcriptase) to 96 well plates containing 25 µL total RNA solution. The RT reaction was carried out by incubation for 30 minutes at 48° C. Following a 10 minute incubation at 95° C. to activate the AMPLITAQ GOLD™, 40 cycles of a two-step PCR protocol were carried out: 95° C. for 15 seconds (denaturation) followed by 60° C. for 1.5 minutes (annealing/extension).

Gene target quantities obtained by real time RT-PCR are normalized using either the expression level of GAPDH, a gene whose expression is constant, or by quantifying total RNA using RiboGreen™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent from Molecular Probes. Methods of RNA quantification by RiboGreen™ are taught in Jones, L. J., et al, *Analytical Biochemistry,* 1998, 265, 368–374.

In this assay, 175 µL of RiboGreen™ working reagent (RiboGreen™ reagent diluted 1:2865 in 10 mM Tris-HCl, 1 mM EDTA, pH 7.5) is pipetted into a 96-well plate containing 25 uL purified, cellular RNA. The plate is read in a CytoFluor 4000 (PE Applied Biosystems) with excitation at 480 nm and emission at 520 nm.

Probes and primers to human cellular apoptosis susceptibility gene were designed to hybridize to a human cellular apoptosis susceptibility gene sequence, using published sequence information (GenBank accession number AF053641, incorporated herein as SEQ ID NO:3). For human cellular apoptosis susceptibility gene the PCR primers were: forward primer: GGAGAATTGTTGAAGAT-GAACCAA (SEQ ID NO: 4) reverse primer: CTGGGCT-GCTAAGCATCAAGT (SEQ ID NO: 5) and the PCR probe was: FAM-TTTGTGAAGCCGATCGAGTGGCC-TAMRA (SEQ ID NO: 6) where FAM (PE-Applied Biosystems, Foster City, Calif.) is the fluorescent reporter dye) and TAMRA (PE-Applied Biosystems, Foster City, Calif.) is the quencher dye. For human GAPDH the PCR primers were: forward primer: CAACGGATTTGGTCGTATTGG (SEQ ID NO: 7)
reverse primer: GGCAACAATATCCACTTTACCAGAGT (SEQ ID NO: 8) and
the PCR probe was: 5' JOE-CGCCTGGTCACCAGGGCTGCT- TAMRA 3' (SEQ ID NO: 9) where JOE (PE-Applied Biosystems, Foster City, Calif.) is the fluorescent reporter dye) and TAMRA (PE-Applied Biosystems, Foster City, Calif.) is the quencher dye.

Example 14

Northern Blot Analysis of Cellular Apoptosis Susceptibility Gene mRNA Levels

Eighteen hours after antisense treatment, cell monolayers were washed twice with cold PBS and lysed in 1 mL RNAZOL™ (TEL-TEST "B" Inc., Friendswood, Tex. ). Total RNA was prepared following manufacturer's recommended protocols. Twenty micrograms of total RNA was fractionated by electrophoresis through 1.2% agarose gels containing 1.1% formaldehyde using a MOPS buffer system (AMRESCO, Inc. Solon, Ohio). RNA was transferred from the gel to HYBOND™-N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER™ UV Crosslinker 2400 (Stratagene, Inc, La Jolla, Calif.) and then robed using QUICKHYB™ hybridization solution (Stratagene, La Jolla, Calif.) using manufacturer's recommendations for stringent conditions.

To detect human cellular apoptosis susceptibility gene, a human cellular apoptosis susceptibility gene specific probe was prepared by PCR using the forward primer GGAGAAT-TGTTGAAGATGAACCAA (SEQ ID NO: 4) and the reverse primer CTGGGCTGCTAAGCATCAAGT (SEQ ID NO: 5). To normalize for variations in loading and transfer efficiency membranes were stripped and probed for human glyceraldehyde-3-phosphate dehydrogenase (GAPDH) RNA (Clontech, Palo Alto, Calif.).

Hybridized membranes were visualized and quantitated using a PHOSPHORIMAGER™ and IMAGEQUANT™ Software V3.3 (Molecular Dynamics, Sunnyvale, Calif.). Data was normalized to GAPDH levels in untreated controls.

Example 15

Antisense Inhibition of Human Cellular Apoptosis Susceptibility Gene Expression by Chimeric Phosphorothioate Oligonucleotides having 2'-MOE Wings and a Deoxy Gap In accordance with the present invention, a series of oligonucleotides were designed to target different regions of the human cellular apoptosis susceptibility gene RNA, using published sequences (GenBank accession number AF053641, incorporated herein as SEQ ID NO: 3, GenBank accession number AF053643, incorporated herein as SEQ ID NO: 10, GenBank accession number AF053644, incorporated herein as SEQ ID NO: 11, GenBank accession number AF053645, incorporated herein as SEQ ID NO: 12, GenBank accession number AF053650, incorporated herein as SEQ ID NO: 13, GenBank accession number AF053640, incorporated herein as SEQ ID NO: 14, and GenBank accession number AF053642, incorporated herein as SEQ ID NO: 15). The oligonucleotides are shown in Table 1. "Target site" indicates the first (5'-most) nucleotide number on the particular target sequence to which the oligonucleotide binds. All compounds in Table 1 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P=S) throughout the oligonucleotide. All cytidine residues are 5-methylcytidines. The compounds were analyzed for their effect on human cellular apoptosis susceptibility gene MRNA levels by quantitative real-time PCR as described in other examples herein. Data are averages from two experiments. If present, "N.D." indicates "no data".

TABLE 1

Inhibition of human cellular apoptosis susceptibility gene mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 128205 | Intron | 10 | 1654 | ggaagaataatacttgtgca | 1 | 16 |
| 128206 | Intron | 11 | 1015 | tcccagcactttgggaggct | 17 | 17 |
| 128207 | Intron | 12 | 2982 | cgaggtatgaagctggacaa | 14 | 18 |
| 128208 | Intron | 12 | 3382 | atgtctccaaatatactgcc | 17 | 19 |
| 128209 | Intron | 12 | 5636 | gcgacattacctgcttctga | 3 | 20 |
| 128210 | Intron | 12 | 6013 | tgaaataaacatcctagttg | 21 | 21 |
| 128211 | Intron | 12 | 9585 | cagggagatcctacagaata | 12 | 22 |
| 128212 | Intron | 13 | 2161 | ggaataaattctgttgataa | 8 | 23 |
| 128213 | 5'UTR | 3 | 3 | aaccccggcaaaatggcgcg | 10 | 24 |
| 128214 | 5'UTR | 3 | 65 | aaccccagccgcggaccgta | 9 | 25 |
| 128215 | Start | 3 | 115 | ctgagttccattgctatagg | 15 | 26 |

TABLE 1-continued

Inhibition of human cellular apoptosis susceptibility gene mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 128216 | Codon Coding | 3 | 202 | agaaatttctcagctggacg | 18 | 27 |
| 128217 | Coding | 3 | 227 | attctgatttccttcaacag | 14 | 28 |
| 128218 | Coding | 3 | 249 | atgtcaaaagcaacagtgga | 13 | 29 |
| 128219 | Coding | 3 | 268 | tcctgggacttctccagtaa | 0 | 30 |
| 128220 | Coding | 3 | 380 | aatggccactcgatcggctt | 33 | 31 |
| 128221 | Coding | 3 | 418 | tctgggctgctaagcatcaa | 0 | 32 |
| 128222 | Coding | 3 | 444 | catcacttaactgcttctga | 13 | 33 |
| 128223 | Coding | 3 | 479 | ctgtggaaaatcttctctgc | 22 | 34 |
| 128224 | Coding | 3 | 491 | gtcaggccatttctgtggaa | 14 | 35 |
| 128225 | Coding | 3 | 500 | tgtcagcaagtcaggccatt | 32 | 36 |
| 128226 | Coding | 3 | 567 | aatgtgctgtacggaggact | 22 | 37 |
| 128227 | Coding | 3 | 590 | atgacggtatctttaaata | 8 | 38 |
| 128228 | Coding | 3 | 679 | atagtggccttaaaaagatt | 16 | 39 |
| 128229 | Coding | 3 | 688 | cagagttcaatagtggcctt | 5 | 40 |
| 128230 | Coding | 3 | 816 | aagtttccatattaccttcc | 25 | 41 |
| 128231 | Coding | 3 | 819 | tccaagtttccatattacct | 15 | 42 |
| 128232 | Coding | 3 | 830 | gaaattattcatccaagttt | 12 | 43 |
| 128233 | Coding | 3 | 900 | gctccaataagccggcttcc | 15 | 44 |
| 128234 | Coding | 3 | 921 | cacaaatctgggattttaag | 21 | 45 |
| 128235 | Coding | 3 | 1069 | gccagaaattgaattgcatt | 14 | 46 |
| 128236 | Coding | 3 | 1118 | gttctggtcctcaaatagat | 33 | 47 |
| 128237 | Coding | 3 | 1173 | cagctctaaattccatgtta | 5 | 48 |
| 128238 | Coding | 3 | 1315 | attcctgtcacaggtccctc | 16 | 49 |
| 128239 | Coding | 3 | 1351 | tattcctgcagcatggaatt | 31 | 50 |
| 128240 | Coding | 3 | 1405 | actaggtagatggctgcatc | 26 | 51 |
| 128241 | Coding | 3 | 1558 | ataccgtcagctttaaggac | 23 | 52 |
| 128242 | Coding | 3 | 1639 | tgaagatgattaatcaagag | 27 | 53 |
| 128243 | Coding | 3 | 1785 | gagctttgaaaaggtttgtt | 23 | 54 |
| 128244 | Coding | 3 | 1837 | ctcatgatagctttcataat | 28 | 55 |
| 128245 | Coding | 3 | 1926 | tcttactaacagctaatagc | 36 | 56 |
| 128246 | Coding | 3 | 1994 | gcaagttattcttatggata | 13 | 57 |
| 128247 | Coding | 3 | 2015 | aacagcagcagggttagctt | 9 | 58 |
| 128255 | Coding | 3 | 2561 | tccaaacattttggttgta | 3 | 59 |
| 128256 | Coding | 3 | 2653 | agtaatttggttatgccaac | 14 | 60 |
| 128257 | Coding | 3 | 2663 | acattctgttagtaatttgg | 13 | 61 |
| 128258 | Coding | 3 | 2795 | tggtgtatcttctatgtcaa | 5 | 62 |
| 128259 | Coding | 3 | 2905 | ttgtgaagtgactgtgccag | 13 | 63 |
| 128260 | Coding | 3 | 2913 | tagacaacttgtgaagtgac | 10 | 64 |
| 128261 | Coding | 3 | 2941 | attgatggaaccccttcctgg | 36 | 65 |
| 128262 | Coding | 3 | 2976 | actggagcgcttctgcattc | 1 | 66 |
| 128263 | Coding | 3 | 2978 | atactggagcgcttctgcat | 25 | 67 |
| 128264 | Stop Codon | 3 | 3028 | aatgcagtttaaagcagtgt | 30 | 68 |
| 128265 | 3'UTR | 3 | 3093 | taatgcagctgtgctcagaa | 36 | 69 |
| 128266 | 3'UTR | 3 | 3160 | agcaacatttaatatcctt | 39 | 70 |
| 128267 | 3'UTR | 3 | 3174 | aaggttcaggttaaagcaac | 18 | 71 |
| 128268 | 3'UTR | 3 | 3196 | acacaaaccaactaatttgc | 23 | 72 |
| 128269 | 3'UTR | 3 | 3222 | gaagccacccacataactgt | 30 | 73 |
| 128270 | 3'UTR | 3 | 3224 | tagaagccacccacataact | 26 | 74 |
| 128271 | 3'UTR | 3 | 3293 | gtgcaaacgctcaacacaaa | 50 | 75 |
| 128272 | 3'UTR | 3 | 3319 | cgtcaaaatttaagattatc | 26 | 76 |
| 128273 | 3'UTR | 3 | 3476 | tgcactgcttggcaagtaac | 18 | 77 |
| 128274 | 3'UTR | 3 | 3496 | agatttgaaactatgaaatg | 36 | 78 |
| 128275 | 3'UTR | 3 | 3504 | ctgattacagatttgaaact | 23 | 79 |
| 128276 | 3'UTR | 3 | 3518 | taggattttattgctgatt | 21 | 80 |
| 128277 | Coding | 14 | 655 | gcattccataccttaaaaag | 17 | 81 |
| 128278 | 3'UTR | 14 | 1460 | aagtccttactggttaatga | 47 | 82 |
| 128279 | 3'UTR | 14 | 1669 | ggagatcttggtgcgccaat | 17 | 83 |
| 128280 | 3'UTR | 14 | 1714 | ccattgatggaacctacagg | 32 | 84 |
| 128281 | Coding | 15 | 624 | atgccttcaaaaataggtcc | 4 | 85 |
| 128282 | 3'UTR | 15 | 787 | gatggaacctacaagagatg | 9 | 86 |

As shown in Table 1, SEQ ID NOs 17, 18, 19, 21, 22, 26, 27, 28, 29, 31, 33, 34, 35, 36, 37, 39, 41, 42, 43, 44, 45, 46, 47, 49, 50, 51, 52, 53, 54, 55, 56, 57, 60, 61, 63, 65, 67, 68, 69, 70, 71, 72, 73, 74, 75, 76, 77, 78, 79, 80, 81, 82, 83 and 84 demonstrated at least 12% inhibition of human cellular apoptosis susceptibility gene expression in this assay and are therefore preferred. The target sites to which these preferred sequences are complementary are herein referred to as "active sites" and are therefore preferred sites for targeting by compounds of the present invention.

Example 16
Western Blot Analysis of Cellular Apoptosis Susceptibility Gene Protein Levels Western blot analysis (immunoblot analysis) is carried out using standard methods. Cells are harvested 16–20 h after oligonucleotide treatment, washed once with PBS, suspended in Laemmli buffer (100 ul/well), boiled for 5 minutes and loaded on a 16% SDS-PAGE gel. Gels are run for 1.5 hours at 150 V, and transferred to membrane for western blotting. Appropriate primary antibody directed to cellular apoptosis susceptibility gene is used, with a radiolabelled or fluorescently labeled secondary antibody directed against the primary antibody species. Bands are visualized using a PHOSPHORIMAGER™ (Molecular Dynamics, Sunnyvale Calif.).

What is claimed is:

1. A compound 8 to 50 nucleobases in length targeted to nucleobases 202 to 2998 of a coding region or nucleobases 3093 to 3538 of a 3'-untranslated region of a nucleic acid molecule encoding human cellular apoptosis susceptibility gene (SEQ ID NO:3), wherein said compound specifically hybridizes with one of said regions and inhibits the expression of human cellular apoptosis susceptibility gene.

2. The compound of claim 1 which is an antisense oligonucleotide.

3. A compound up to 50 nucleobases in length consisting of at least an 8-nucleobase portion of SEQ ID NO: 17, 18, 19, 21, 22, 26, 27, 28, 29, 31, 33, 34, 35, 36, 37, 39, 41, 42, 43, 44, 45, 46, 47, 49, 50, 51, 52, 53, 54, 55, 56, 57, 60, 61, 63, 65, 67, 68, 69, 70, 71, 72, 73, 74, 75, 76, 77, 78, 79, 80, 81, 82, 83 or 84 which inhibits the expression of humane cellular apoptosis susceptibility gene.

4. The compound of claim 2 wherein the antisense oligonucleotide comprises at least one modified internucleoside linkage.

5. The compound of claim 4 wherein the modified internucleoside linkage is a phosphorbthioate linkage.

6. The compound of claim 2 wherein the antisense oligonucleotide comprises at least one modified sugar moiety.

7. The compound of claim 6 wherein the modified sugar moiety is a 2'-O-methoxyethyl sugar moiety.

8. The compound of claim 2 wherein the antisense oligonucleotide comprises at least one modified nucleobase.

9. The compound of claim 8 wherein the modified nucleobase is a 5-methylcytosine.

10. The compound of claim 2 wherein the antisense oligonucleotide is a chimeric oligonucleotide.

11. A composition comprising the compound of claim 1 and a pharmaceutically acceptable carrier or diluent.

12. The composition of claim 11 further comprising a colloidal dispersion system.

13. The composition of claim 11 wherein the compound is an antisense oligonucleotide.

14. A method of inhibiting the expression of human cellular apoptosis susceptibility gene in cells or tissues comprising contacting said cells or tissues in vitro with the compound of claim 1 so that expression of human cellular apoptosis susceptibility gene is inhibited.

15. The compound of claim 3 which is an antisense oligonucleotide.

16. The compound of claim 15 wherein the antisense oligonucleotide comprises at least one modified internucleoside linkage.

17. The compound of claim 16 wherein the modified internucleoside linkage is a phosphorothioate linkage.

18. The compound of claim 15 wherein the antisense oligonucleotide comprises at least one modified sugar moiety.

19. The compound of claim 18 wherein the modified sugar moiety is a 2'-O-methoxyethyl sugar moiety.

20. The compound of claim 15 wherein the antisense oligonucleotide comprises at least one modified nucleobase.

21. The compound of claim 20 wherein the modified nucleobase is a 5-methylcytosine.

22. The compound of claim 15 wherein the antisense oligonucleotide is a chimeric oligonucleotide.

23. A composition comprising the compound of claim 3 and a pharmaceutically acceptable carrier or diluent.

24. The composition of claim 23 further comprising a colloidal dispersion system.

25. The composition of claim 23 wherein the compound is an antisense oligonucleotide.

26. A method of inhibiting the expression of cellular apoptosis susceptibility gene in human cells or tissues comprising contacting said cells or tissues in vitro with the compound of claim 3 so that expression of human cellular apoptosis gene cellular is inhibited.

* * * * *

SEQUENCE LISTING

<160> NUMBER OF SEQ ID NOS: 86

<210> SEQ ID NO 1
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 1
tccgtcatcg ctcctcaggg                                                    20

<210> SEQ ID NO 2
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 2
atgcattctg cccccaagga                                                    20

<210> SEQ ID NO 3
<211> LENGTH: 3569
<212> TYPE: DNA
<213> ORGANISM: Homo sapiens
<220> FEATURE:
<223> OTHER INFORMATION:
<221> NAME/KEY: unsure
<222> LOCATION: 3356
<223> OTHER INFORMATION: unknown
<221> NAME/KEY: CDS
<222> LOCATION: (124)...(3039)

<400> SEQUENCE: 3
gtcgcgccat tttgccgggg tttgaatgtg aggcggagcg gcggcaggag cggatagtgc        60
cagctacggt ccgcggctgg ggttccctcc tccgtttctg tatccccacg agatcctata       120 gca atg gaa ctc agc gat gca aat ctg caa aca cta aca gaa tat tta        168
    Met Glu Leu Ser Asp Ala Asn Leu Gln Thr Leu Thr Glu Tyr Leu
     1               5                  10                  15 aag aaa aca ctt gat cct gat cct gcc atc cga cgt cca gct gag aaa        216
Lys Lys Thr Leu Asp Pro Asp Pro Ala Ile Arg Arg Pro Ala Glu Lys
                 20                  25                  30 ttt ctt gaa tct gtt gaa gga aat cag aat tat cca ctg ttg ctt ttg        264
Phe Leu Glu Ser Val Glu Gly Asn Gln Asn Tyr Pro Leu Leu Leu Leu
             35                  40                  45 aca tta ctg gag aag tcc cag gat aat gtt atc aaa gta tgt gct tca        312
Thr Leu Leu Glu Lys Ser Gln Asp Asn Val Ile Lys Val Cys Ala Ser
         50                  55                  60 gta aca ttc aaa aac tat att aaa agg aac tgg aga att gtt gaa gat        360
Val Thr Phe Lys Asn Tyr Ile Lys Arg Asn Trp Arg Ile Val Glu Asp
     65                  70                  75 gaa cca aac aaa att tgt gaa gcc gat cga gtg gcc att aaa gcc aac        408
Glu Pro Asn Lys Ile Cys Glu Ala Asp Arg Val Ala Ile Lys Ala Asn
 80                  85                  90                  95 ata gtg cac ttg atg ctt agc agc cca gag caa att cag aag cag tta        456

-continued

```
Ile Val His Leu Met Leu Ser Ser Pro Glu Gln Ile Gln Lys Gln Leu
            100                 105                 110 agt gat gca att agc att att ggc aga gaa gat ttt cca cag aaa tgg      504
Ser Asp Ala Ile Ser Ile Ile Gly Arg Glu Asp Phe Pro Gln Lys Trp
            115                 120                 125 cct gac ttg ctg aca gaa atg gtg aat cgc ttt cag agt gga gat ttc      552
Pro Asp Leu Leu Thr Glu Met Val Asn Arg Phe Gln Ser Gly Asp Phe
            130                 135                 140 cat gtt att aat gga gtc ctc cgt aca gca cat tca tta ttt aaa aga      600
His Val Ile Asn Gly Val Leu Arg Thr Ala His Ser Leu Phe Lys Arg
145                 150                 155 tac cgt cat gaa ttt aag tca aac gag tta tgg act gaa att aag ctt      648
Tyr Arg His Glu Phe Lys Ser Asn Glu Leu Trp Thr Glu Ile Lys Leu
160                 165                 170                 175 gtt ctg gat gcc ttt gct ttg cct ttg act aat ctt ttt aag gcc act      696
Val Leu Asp Ala Phe Ala Leu Pro Leu Thr Asn Leu Phe Lys Ala Thr
            180                 185                 190 att gaa ctc tgc agt acc cat gca aat gat gcc tct gcc ctg agg att      744
Ile Glu Leu Cys Ser Thr His Ala Asn Asp Ala Ser Ala Leu Arg Ile
            195                 200                 205 ctg ttt tct tcc ctg atc ctg atc tca aaa ttg ttc tat agt tta aac      792
Leu Phe Ser Ser Leu Ile Leu Ile Ser Lys Leu Phe Tyr Ser Leu Asn
            210                 215                 220 ttt cag gat ctc cct gaa ttt tgg gaa ggt aat atg gaa act tgg atg      840
Phe Gln Asp Leu Pro Glu Phe Trp Glu Gly Asn Met Glu Thr Trp Met
            225                 230                 235 aat aat ttc cat act ctc tta aca ttg gat aat aag ctt tta caa act      888
Asn Asn Phe His Thr Leu Leu Thr Leu Asp Asn Lys Leu Leu Gln Thr
240                 245                 250                 255 gat gat gaa gag gaa gcc ggc tta ttg gag ctc tta aaa tcc cag att      936
Asp Asp Glu Glu Glu Ala Gly Leu Leu Glu Leu Leu Lys Ser Gln Ile
            260                 265                 270 tgt gat aat gcc gca ctc tat gca caa aag tac gat gaa gaa ttc cag      984
Cys Asp Asn Ala Ala Leu Tyr Ala Gln Lys Tyr Asp Glu Glu Phe Gln
            275                 280                 285 cga tac ctg cct cgt ttt gtt aca gcc atc tgg aat tta cta gtt aca     1032
Arg Tyr Leu Pro Arg Phe Val Thr Ala Ile Trp Asn Leu Leu Val Thr
            290                 295                 300 acg ggt caa gag gtt aaa tat gat ttg ttg gta agt aat gca att caa     1080
Thr Gly Gln Glu Val Lys Tyr Asp Leu Leu Val Ser Asn Ala Ile Gln
305                 310                 315 ttt ctg gct tca gtt tgt gag aga cct cat tat aag aat cta ttt gag     1128
Phe Leu Ala Ser Val Cys Glu Arg Pro His Tyr Lys Asn Leu Phe Glu
320                 325                 330                 335 gac cag aac acg ctg aca agt atc tgt gaa aag gtt att gtg cct aac     1176
Asp Gln Asn Thr Leu Thr Ser Ile Cys Glu Lys Val Ile Val Pro Asn
            340                 345                 350 atg gaa ttt aga gct gct gat gaa gaa gca ttt gaa gat aat tct gag     1224
Met Glu Phe Arg Ala Ala Asp Glu Glu Ala Phe Glu Asp Asn Ser Glu
            355                 360                 365 gag tac ata agg aga gat ttg gaa gga tct gat att gat act aga cgc     1272
Glu Tyr Ile Arg Arg Asp Leu Glu Gly Ser Asp Ile Asp Thr Arg Arg
            370                 375                 380 agg gct gct tgt gat ctg gta cga gga tta tgc aag ttt ttt gag gga     1320
Arg Ala Ala Cys Asp Leu Val Arg Gly Leu Cys Lys Phe Phe Glu Gly
385                 390                 395 cct gtg aca gga atc ttc tct ggt tat gtt aat tcc atg ctg cag gaa     1368
Pro Val Thr Gly Ile Phe Ser Gly Tyr Val Asn Ser Met Leu Gln Glu
400                 405                 410                 415
```

-continued

| | |
|---|---|
| tac gca aaa aat cca tct gtc aac tgg aaa cac aaa gat gca gcc atc<br>Tyr Ala Lys Asn Pro Ser Val Asn Trp Lys His Lys Asp Ala Ala Ile<br>420                     425                  430 | 1416 |
| tac cta gtg aca tct ttg gca tca aaa gcc caa aca cag aag cat gga<br>Tyr Leu Val Thr Ser Leu Ala Ser Lys Ala Gln Thr Gln Lys His Gly<br>            435                  440                  445 | 1464 |
| att aca caa gca aat gaa ctt gta aac cta act gag ttc ttt gtg aat<br>Ile Thr Gln Ala Asn Glu Leu Val Asn Leu Thr Glu Phe Phe Val Asn<br>450                     455                  460 | 1512 |
| cac atc ctc cct gat tta aaa tca gct aat gtg aat gaa ttt cct gtc<br>His Ile Leu Pro Asp Leu Lys Ser Ala Asn Val Asn Glu Phe Pro Val<br>465                     470                  475 | 1560 |
| ctt aaa gct gac ggt atc aaa tat att atg att ttt aga aat caa gtg<br>Leu Lys Ala Asp Gly Ile Lys Tyr Ile Met Ile Phe Arg Asn Gln Val<br>480                  485                  490                  495 | 1608 |
| cca aaa gaa cat ctt tta gtc tcg att cct ctc ttg att aat cat ctt<br>Pro Lys Glu His Leu Leu Val Ser Ile Pro Leu Leu Ile Asn His Leu<br>            500                  505                  510 | 1656 |
| caa gct gga agt att gtt gtt cat act tac gca gct cat gct ctt gaa<br>Gln Ala Gly Ser Ile Val Val His Thr Tyr Ala Ala His Ala Leu Glu<br>               515                  520                  525 | 1704 |
| cgg ctc ttt act atg cga ggg cct aac aat gcc act ctc ttt aca gct<br>Arg Leu Phe Thr Met Arg Gly Pro Asn Asn Ala Thr Leu Phe Thr Ala<br>            530                  535                  540 | 1752 |
| gca gaa atc gca ccg ttt gtt gag att ctg cta aca aac ctt ttc aaa<br>Ala Glu Ile Ala Pro Phe Val Glu Ile Leu Leu Thr Asn Leu Phe Lys<br>545                     550                  555 | 1800 |
| gct ctc aca ctt cct ggc tct tca gaa aat gaa tat att atg aaa gct<br>Ala Leu Thr Leu Pro Gly Ser Ser Glu Asn Glu Tyr Ile Met Lys Ala<br>560                     565                  570                  575 | 1848 |
| atc atg aga agt ttt tct ctc cta caa gaa gcc ata atc ccc tac atc<br>Ile Met Arg Ser Phe Ser Leu Leu Gln Glu Ala Ile Ile Pro Tyr Ile<br>                   580                  585                  590 | 1896 |
| cct act ctc atc act cag ctt aca cag aag cta tta gct gtt agt aag<br>Pro Thr Leu Ile Thr Gln Leu Thr Gln Lys Leu Leu Ala Val Ser Lys<br>            595                  600                  605 | 1944 |
| aac cca agc aaa cct cac ttt aat cac tac atg ttt gaa gca ata tgt<br>Asn Pro Ser Lys Pro His Phe Asn His Tyr Met Phe Glu Ala Ile Cys<br>            610                  615                  620 | 1992 |
| tta tcc ata aga ata act tgc aaa gct aac cct gct gct gtt gta aat<br>Leu Ser Ile Arg Ile Thr Cys Lys Ala Asn Pro Ala Ala Val Val Asn<br>625                     630                  635 | 2040 |
| ttt gag gag gct ttg ttt ttg gtg ttt act gaa atc tta caa aat gat<br>Phe Glu Glu Ala Leu Phe Leu Val Phe Thr Glu Ile Leu Gln Asn Asp<br>640                     645                  650                  655 | 2088 |
| gtg caa gaa ttt att cca tac gtc ttt caa gtg atg tct ttg ctt ctg<br>Val Gln Glu Phe Ile Pro Tyr Val Phe Gln Val Met Ser Leu Leu Leu<br>            660                  665                  670 | 2136 |
| gaa aca cac aaa aat gac atc ccg tct tcc tat atg gcc tta ttt cct<br>Glu Thr His Lys Asn Asp Ile Pro Ser Ser Tyr Met Ala Leu Phe Pro<br>               675                  680                  685 | 2184 |
| cat ctc ctt cag cca gtg ctt tgg gaa aga aca gga aat att cct gct<br>His Leu Leu Gln Pro Val Leu Trp Glu Arg Thr Gly Asn Ile Pro Ala<br>            690                  695                  700 | 2232 |
| cta gtg agg ctt ctt caa gca ttc tta gaa cgc ggt tca aac aca ata<br>Leu Val Arg Leu Leu Gln Ala Phe Leu Glu Arg Gly Ser Asn Thr Ile<br>705                     710                  715 | 2280 |
| gca agt gct gca gct gac aaa att cct ggg tta cta ggt gtc ttt cag<br>Ala Ser Ala Ala Ala Asp Lys Ile Pro Gly Leu Leu Gly Val Phe Gln<br>720                     725                  730                  735 | 2328 |

-continued

| | |
|---|---|
| aag ctg att gca tcc aaa gca aat gac cac caa ggt ttt tat ctt cta<br>Lys Leu Ile Ala Ser Lys Ala Asn Asp His Gln Gly Phe Tyr Leu Leu<br>              740                  745                  750 | 2376 |
| aac agt ata ata gag cac atg cct cct gaa tca gtt gac caa tat agg<br>Asn Ser Ile Ile Glu His Met Pro Pro Glu Ser Val Asp Gln Tyr Arg<br>              755                  760                  765 | 2424 |
| aaa caa atc ttc att ctg cta ttc cag aga ctt cag aat tcc aaa aca<br>Lys Gln Ile Phe Ile Leu Leu Phe Gln Arg Leu Gln Asn Ser Lys Thr<br>              770                  775                  780 | 2472 |
| acc aag ttt atc aag agt ttt tta gtc ttt att aat ttg tat tgc ata<br>Thr Lys Phe Ile Lys Ser Phe Leu Val Phe Ile Asn Leu Tyr Cys Ile<br>785                  790                  795 | 2520 |
| aaa tat ggg gca cta gca cta caa gaa ata ttt gat ggt ata caa cca<br>Lys Tyr Gly Ala Leu Ala Leu Gln Glu Ile Phe Asp Gly Ile Gln Pro<br>800                  805                  810                  815 | 2568 |
| aaa atg ttt gga atg gtt ttg gaa aaa att att att cct gaa att cag<br>Lys Met Phe Gly Met Val Leu Glu Lys Ile Ile Ile Pro Glu Ile Gln<br>              820                  825                  830 | 2616 |
| aag gta tct gga aat gta gag aaa aag atc tgt gcg gtt ggc ata acc<br>Lys Val Ser Gly Asn Val Glu Lys Lys Ile Cys Ala Val Gly Ile Thr<br>              835                  840                  845 | 2664 |
| aaa tta cta aca gaa tgt ccc cca atg atg gac act gag tat acc aaa<br>Lys Leu Leu Thr Glu Cys Pro Pro Met Met Asp Thr Glu Tyr Thr Lys<br>              850                  855                  860 | 2712 |
| ctg tgg act cca tta tta cag tct ttg att ggt ctt ttt gag tta ccc<br>Leu Trp Thr Pro Leu Leu Gln Ser Leu Ile Gly Leu Phe Glu Leu Pro<br>865                  870                  875 | 2760 |
| gaa gat gat acc att cct gat gag gaa cat ttt att gac ata gaa gat<br>Glu Asp Asp Thr Ile Pro Asp Glu Glu His Phe Ile Asp Ile Glu Asp<br>880                  885                  890                  895 | 2808 |
| aca cca gra tat cag act gcc ttc tca cag ttg gca ttt gct ggg aaa<br>Thr Pro Xaa Tyr Gln Thr Ala Phe Ser Gln Leu Ala Phe Ala Gly Lys<br>              900                  905                  910 | 2856 |
| aaa gag cat gat cct gta ggt caa atg gtg aat aac ccc aaa att cac<br>Lys Glu His Asp Pro Val Gly Gln Met Val Asn Asn Pro Lys Ile His<br>              915                  920                  925 | 2904 |
| ctg gca cag tca ctt cac aag ttg tct acc gcc tgt cca gga agg gtt<br>Leu Ala Gln Ser Leu His Lys Leu Ser Thr Ala Cys Pro Gly Arg Val<br>              930                  935                  940 | 2952 |
| cca tca atg gtg agc acc agc ctg aat gca gaa gcg ctc cag tat ctc<br>Pro Ser Met Val Ser Thr Ser Leu Asn Ala Glu Ala Leu Gln Tyr Leu<br>945                  950                  955 | 3000 |
| caa ggg tac ctt cag gca gcc agt gtg aca ctg ctt taa actgcatttt<br>Gln Gly Tyr Leu Gln Ala Ala Ser Val Thr Leu Leu<br>960                  965                  970 | 3049 |
| tctaatgggc taaacccaga tggtttccta ggaaatcaca ggcttctgag cacagctgca | 3109 |
| ttaaaacaaa ggaagttctc cttttgaact tgtcacgaat tccatcttgt aaaggatatt | 3169 |
| aaatgttgct ttaacctgaa ccttgagcaa attagttggt ttgtgtgatc atacagttat | 3229 |
| gtgggtggct tctagtttgc aacttcaagg gacaagtatt aatagttcag tgtatggcgt | 3289 |
| tggtttgtgt tgagcgtttg cacggtttgg ataatcttaa attttgacgg acactgtgga | 3349 |
| gactttnctg ttactaaatc cttttgtttt gaagctgttg ctatttgtat ttctcttgtc | 3409 |
| ctttatattt tttgtctgtt tatttacgct tttattggaa atgtgaataa gtaaagaatt | 3469 |
| acttgtgtta cttgccaagc agtgcacatt tcatagtttc aaatctgtaa tcagcaataa | 3529 |
| aaatcctaaa atatgtacct aaaaaaaaaa aaaaaaaaa | 3569 |

<210> SEQ ID NO 4
<211> LENGTH: 24
<212> TYPE: DNA
<213> ORGANISM: Artificial Sequence
<220> FEATURE:
<223> OTHER INFORMATION: PCR Primer

<400> SEQUENCE: 4
ggagaattgt tgaagatgaa ccaa                                              24

<210> SEQ ID NO 5
<211> LENGTH: 21
<212> TYPE: DNA
<213> ORGANISM: Artificial Sequence
<220> FEATURE:
<223> OTHER INFORMATION: PCR Primer

<400> SEQUENCE: 5
ctgggctgct aagcatcaag t                                                 21

<210> SEQ ID NO 6
<211> LENGTH: 23
<212> TYPE: DNA
<213> ORGANISM: Artificial Sequence
<220> FEATURE:
<223> OTHER INFORMATION: PCR Probe

<400> SEQUENCE: 6
tttgtgaagc cgatcgagtg gcc                                               23

<210> SEQ ID NO 7
<211> LENGTH: 21
<212> TYPE: DNA
<213> ORGANISM: Artificial Sequence
<220> FEATURE:
<223> OTHER INFORMATION: PCR Primer

<400> SEQUENCE: 7
caacggattt ggtcgtattg g                                                 21

<210> SEQ ID NO 8
<211> LENGTH: 26
<212> TYPE: DNA
<213> ORGANISM: Artificial Sequence
<220> FEATURE:
<223> OTHER INFORMATION: PCR Primer

<400> SEQUENCE: 8
ggcaacaata tccactttac cagagt                                            26

<210> SEQ ID NO 9
<211> LENGTH: 21
<212> TYPE: DNA
<213> ORGANISM: Artificial Sequence
<220> FEATURE:
<223> OTHER INFORMATION: PCR Probe

<400> SEQUENCE: 9
cgcctggtca ccagggctgc t                                                 21

<210> SEQ ID NO 10
<211> LENGTH: 2929
<212> TYPE: DNA
<213> ORGANISM: Homo sapiens

<400> SEQUENCE: 10

-continued

```
gtcgcgccat tttgccgggg tttgaatgtg aggcggagcg gcggcaggag cgggtagtgc    60
cagctacggt ccgcggctgg ggttcctcct ccgtttctgt atccccacga ggtgaggcgc   120
ggggcgtgca cggcctacca gagtggctct tggggcccag ctgaggaagg gatgaggcgc   180
tcccggtact aacgagcgct agggagtgag aaccgcgcct ctgggcgaga gcggaatgtg   240
ggcccggggt tcgggtggtg cgctcaggca aggtcttcgg cttccctagg gagcgcttgc   300
cgcgcctcgc ggcatcctag gtctctggcc caggtgcggc gaccccaggg cctgtgaggg   360
ctgagggcaa ctgaggcgcg gcctaacgcg agcctgcgga ttgcccgccc tttcctctcc   420
atcacgcgc tgattggctg cgccgccgcc tctccgctcg ggaaggccgc tccttattgg    480
tcgcgctcgc atgtccattc tctgcgacgg tggctgctag ccgcgcgagc tgagtgtgcg   540
gcggcgtggc ctgcccgggc ggggtctgcg ggcgcgtgga gctgcggctg cctcgcgtcg   600
tcccttgccc taactctagt gaagcccccg tcgtgatctc actttgctga attgtttgtg   660
agaattctag tcggtacacc cggacatag aaatcccctg taacgcgggt tggggagggg    720
ttccctcgtt tgggagaaa cgctgtgctg tggtggttcg gagcatagac tttgaatta    780
gatcgcctgg gttcattcca gacgtagcct ctcgttaggg gtgtaacttg aggctggtca   840
cctcatctca ctgagcctcc atttccttag ctgcaaaatg gggttaataa cagaatctac   900
ctcggaaagt ggctttgagg atgcgctgag ttatttaccg tggtttacaa aggttccctg   960
ggagctgacg gttgtttatt catctctccc acccatcttt ctccttagcc agtgtggctt  1020
tctgtttctt ccatattcca gggttattcc gatttaaaat tatttgcaca tgccttttgt  1080
ttgctgggga agtaccaaca tttttgcaag gcaggccgcc tctcccaagt ttccctcacc  1140
ttaggcctcc cctaaccaac ctcttctttt gttttctttt tcttttcctt ttctcttttc  1200
tttttttttt tttttttttt tttttttttg agagagagag tctcgctctg cctcccaggc  1260
tggagtgcag tggcgcgatc tcgactcaat gcaacctccg cctcccggat tcaagcgatt  1320
ttcctgcctc agcctcccga atagctgaga ctacaggtct gagaatacac gccaccacac  1380
ccggctaatt tttgtatttt tattagagac ggggtttcac catgttgatc aggctgtcta  1440
atcaacctgt ttaggacctt tctcccatgg ctctccatca acatcacctg gttttagtta  1500
cttcatagca tttactaaca cttacttatt gcttacttgt tatctttctc aactgctaga  1560
atgtaagctg tttgagagca aggaccttgt ctgtcttgct tacttctctc tccctggtgg  1620
gtgccatccc acctgtgctt gccacatggt agatgcacaa gtattattct tccttggagg  1680
cacagaaggg gacccttag tcttggattc caccaattgc tctttttctc accttgggcc   1740
cacatagtca tatctttggc ctttctctgt gtgtgtctct ctctttttt tttttttttt   1800
tgacatgctt tcagaggatc ctaatggacc tcgtctctcc gctcctacaa ccctttatct  1860
ttcacttctt accatcagtg caagggaagt ctctctcccc ttctgattac ttctgctggt  1920
tggggtctgg gacaggattg gatggatgca agagcagtgc tctagttttg gaattaattt  1980
gtttctttat tcatttaata actttattga gcatccactt aatctctggg aatatagtga  2040
aaaaacaaaa atggacaagg tcccttccct tgaggaccat gtattctcgt gggcgaaaga  2100
aaaaacatta gataatttca gatagtgaca gaattatgtg acaggtgaag aaggcttttc  2160
tgaggaggtg acatttgggt agagaccagc cattaaaagg tgaggggcag aacattccag  2220
gtagagggaa tagaaggctc aaggctcaag gacaggaacc ggcttggaat attgaaatat  2280
ttaaggaata ttttaggttc ctagagtgtt acatgaagaa gggagaaata tccaggaccc  2340
```

-continued

```
ggatcataga aggctttgta ggcaatgtaa ggagtttgga tttgattcta agtggtatat    2400
tcctatggtt agaaagcaga gggtaggttg aggtgttggg atatgttctt catgtgtggg    2460
tgccagatag acctcattca ttggatctct ttccctcttc ccaaacgtaa ggcatcggga    2520
atggttctct aatgtgtaga ggacatatct aagaaaaags cagacatctt ggatcagctt    2580
atgtcacaga tgtctgtgag atggctttgg aaaacaaagc tttttattcc agaaatctcc    2640
acctgtaatt gagggcctgt gggaagatgc tagacttagg tctggccatt cattcaacaa    2700
gaagaacttg gaaatttaga tgtctgccat aactgattta ttgtgatgct ttttttaagtt   2760 tcttaattgt gtattggtag agatttccaa agatagttac gtggagaaag aaaagtatca    2820 cccctcatt taaaggtgat aaaaatgaat tcttatcttc tccctccctt ttttttttgg     2880
agacaccagc tcactgtgtt gcctgggctg acctgggctc agtctatcc                2929
```

<210> SEQ ID NO 11
<211> LENGTH: 3609
<212> TYPE: DNA
<213> ORGANISM: Homo sapiens
<220> FEATURE:
<223> OTHER INFORMATION:
<221> NAME/KEY: unsure
<222> LOCATION: 92
<223> OTHER INFORMATION: unknown
<221> NAME/KEY: unsure
<222> LOCATION: 869
<223> OTHER INFORMATION: unknown
<221> NAME/KEY: unsure
<222> LOCATION: 1385
<223> OTHER INFORMATION: unknown

<400> SEQUENCE: 11

```
tgtgtgtgtg tgtgtggtga aagcacttaa aatataccca gtaattttca agtgtacaat    60
acattattat agtcaccttg ttgtacaata antctcttga actgtgtatt tcttagccta    120
tgttgttagt agttaaatcg acgtaggcca tctagttagc ttaaaatttg tgggctgggc    180
acggtggctc acgcctgtaa tcctagcaca ctgggaggcc aaggcaggag gatcacttga    240
gtccaggagt ttgagaccag cttgggcaac attgtgagac cctgtctcta caaaattttt    300
tttttaattt gtcatctgtt agatgtgaag ttttttggtc agttataagc atattatgtg    360
atttagtttt gtttaagctt taaatatgaa aacttctaga atcataatct tagcttgtca    420
tcttctgaac tctagaattt atctccctag atgcaaattc ttagcacttt gtagtatttg    480
cgattacatg ttgtacatga aggaatttct tgtttcttta atctcagaac tttatgtggg    540
atatttattt gctgtttaaa atttaatttt ctcgttgtgg ggccttttt tttttttttt     600 ttaagacagg tcttgctcca tcacccaagt tggagtgcag tggcaccatc tcagctcact    660
gcaacctctg cccccaggct caagacatct tcccacctca gccttccgag tagctgggac    720
tgaaggcacc cactaccatg cctggctaat ttttggggtt ggttggttgg tttgttttga    780
gacggagttt tgctcttatc gcccaggctg cagtgctatg gtcgatctc agctcactga     840 aacctttgcc tcccgggttc aagcgattnt cctgcctcag cctccacaag tagctgagat    900
tacaggctcc tgccaccatg tccagctaat ttttgtattt ttagtagaga cgggatttta    960
ccatgttgac caggttggtc tcaaattctt gacctcaggt gatccgcctg cctcagcctc    1020
ccaaagtgct gggattacag gcatgagcca ccatgcccgg cttaattttt tttgtagttt    1080
tggtagagat ggggtctcac cctgttgaca ggctggtctc ttaactcgtg agctcaagca    1140
gtccacccac ctcagcctcc caaagtgtcg ggatttacag gcctgagcca ctgccgggc    1200
```

-continued

```
tccttatggg gcttctttaa taagttcctc cagtgatttt ttttttctta acctttatta    1260
gcccttcccc atagcattaa atcatataaa cttcttggtg acttggagca gtccttcagc    1320
ttttttttct aggactatct ttttgaaatt ttgggatttt tttcatttc ccttatcaca     1380
aaatngtctc actattgttt ttgggggaaa aggcacattt catttgctgg attctttttt    1440
cagagtcagg tttactgccc acctaaaaaa aacagatgg atgactttca gagagaataa     1500
cccataatat aaacggattt ctttaaatgt aaatcacttt ttccgtaagt gaccagttat    1560
ccacacctta ttttatattt tagatcctat agcaatggaa ctcagcgatg caaatctgca    1620
aacactaaca gaatatttaa agaaaacact tgatcctgat cctgccatcc gacgtccagg    1680
taaagaaaat aaacgttttt tggttgatta attccttcag gacaggtgag agaaacctat    1740
gtattatctg cctccttata aatatatttt aaaaaattca tacttgggtt ctcaagcgta    1800
gtttataagt gttacagctg ctataccatg gtgtgttgtt tctttttga gttaaaatag     1860
cttttatttg gcatcttcct gggattaaaa agtactagtt ttcggataaa aagtactgac    1920
atgtttagaa tgctttgttc tttgacctt tcaaaatacc cacttaaaac atgcctgctt     1980
taggccggat gcggtggctc acacctgtaa tcccagcact ttgggaggct gaggcaggcg    2040
gatcacgacg tcaggagatg gagaccatcc tggctaacac ggtgaaaccc cgtctctact    2100
aaaagtacaa aaaattagcc aggcgtggtg gcgggtgcct gtggtcccag ctactcagga    2160
ggctgagtca ggagaatggc gtgaaccccg gaggcagagc ttgcagtgag ccgagattgc    2220
gccactgcac tccagcctgg gcgacagagc aagactccgt ctcaaaaaaa aaaaaaagcc    2280
tgctttagag ataaaataat tagggcatag aaaggagagt aattgcctaa aaagtgatta    2340
agtgaatgaa gccaagtaat cagttactgt ctcttaattt taattttcta ttgggtttga    2400
tttaactaat atattttaag acctagagct ttttttttcc ttcctgaatc tgaccagatt    2460
ccattaaaaa cgtagaatta aaatattgaa ctcaggtgtt cacaggactc agctgttaag    2520
ttaaatgagg gagataggcc aagtggagac tggtaatatc aggagaatac atgccctgat    2580
taagtggcaa gtacttttg gaactagcta attttgggga ttcagactag ttttgcaaga    2640
tcagatttcc agttttgctt gaaaaataag gatatttata tgaagtgccc tcattttaa    2700
atgttagcaa gtaacttcaa aagatttggg gccgggtgc ggtggctcac gcttgtaatc     2760
ccagcacttt gggaggccga ggtgggcaga tcacgagggc aggagatcga gaccatcgtg    2820
gctaatatgg tgaaacccct tctttactaa aaatacaaa aacttagctg ggtgtgatgg     2880
cacacacctg tagtcccagc tgctcaagag gctgaggcag gagaattgct tgaacctggg    2940
aggtggaggt tgcagtgagt tgagattgcg ccactgcact ccagcctggg tgacagagcg    3000
agacgtagtc ccaaaaaaaa aaatattttg aaacacagcc agggttggtg gtcacgcctt    3060
taatcccagt aatttgggag gccaaggcag gaagatccct tgagtccagg agttcgagac    3120
cagcctgggc aacaaagcaa gaccctgtct ctacaaaaaa tttaaaaatt agccaagtgt    3180
ggtgatgtgt gcctgtattc ctagcaactg ggaggctga acaaaagct tccttataac      3240
aagaggtcgg agctgcagtg agttatgatc atgtcagtgc actctagcct gggtgacaga    3300
gggaaatctt gtcttaaaaa aaaaaaaaaa aaggccaggt gcatttgctc acgcctgtaa    3360
tcccagcatt ttgggaagcc aaggcaggcg gatcatgagg tcaagagatc tagaccatcc    3420
tggccaatgt ggtgaaaccc tgtctctact aaaaatacaa aaattagctg ggcgtggtgg    3480
tgcacggctg tagtcccaga tacttgggag gctgaggcag gagaattgct tgaatccagg    3540
aagcggaggt tgcagttaac cgaggccact gcactccagc ctggtgacag agcaagactc    3600
```

-continued cgtctcaaa                                                                3609

<210> SEQ ID NO 12
<211> LENGTH: 12597
<212> TYPE: DNA
<213> ORGANISM: Homo sapiens
<220> FEATURE:
<223> OTHER INFORMATION:
<221> NAME/KEY: unsure
<222> LOCATION: 4964
<223> OTHER INFORMATION: unknown
<221> NAME/KEY: unsure
<222> LOCATION: 7633
<223> OTHER INFORMATION: unknown

<400> SEQUENCE: 12

```
ctacttggga ggctgaggtg caagaatcgc ttgaacccag gaggtgaagg ttccagtgag     60
ccaagattgc ccaactgcac tccagcctag gtgacagagt gagactttgt ctcaaaaaaa    120
aaaaaaattg aaatacagtg caagccaaac tacttctggg ccagatatat cttgtgagca    180
gtcagttatt gatccttgat atgggccata ttaaaatgct cttgacctgt ttcttcaaaa    240
cttaccaatg tgcatgctca tagaggatgt tggaagggtt ccatgaggaa gagaatgtgt    300
gttatatatt atgtatgatg actagaatca tgaacatgtt aatgcatcta tcctcttcta    360
gaaaagtatt tgtgattttt gagaggtaaa attagtttat tagtgtataa agaagtaatg    420
tgttcctgga taagggaag ttaatggctc taatctttaa tcttcttaga cttttcaaaga    480
aagctgttgc caacactatt aaaaaatttt tttttttttt tttttttgga gacggagtct    540
ccctctgtcg cccaggctag agtgcagtgg cgccatcttg gctcactgca agctccgcct    600
cccgggtcca cgccattctc ctgcctcagc ctcctgagta gctgggacta caggcgcccg    660
ccaccatgcc tacctaatta tttgtatttt tagtagagac agggtttcac cgtgttagcc    720
aggatggtct ccatctccat gacctcgtga tccacccgcc tcagccgtcc caaagtgctg    780
ggattacagg catgagccgt gcccggtgga aaaattatta ttattattta tttatttat    840
tatttatttta tttattttg agacagagtc tcactcttgc ccaggctgga gtgcagtggc    900
gccatcttgg ctcactgcaa gctccacctc ccgggttcac cccattgttg tgcctcagcc    960
tcccgagtag ctgggactaa ggcgcccgcc accacacccg gctaatttttt tgtattttta   1020
gtagagacgg gtgtttcacc aggttagtca ggatggtctc gatttcctga ccttgtgatc   1080
cactcgtctc ggcctcccat agtgctggga ttacaggtgt gagccaccgc acccggcaat   1140
tatttttttt ttaataatgt gtgaggcaag agttctgttg ctttatgtat tcaggacaga   1200
gtataaaaat aatctggtat ttctggaagt taggacatag catttctcag ggatcgagac   1260
tgactgacta gactgactca actagaccct ttgagactcc ttgagtgcgc agaaacatat   1320
gcatgtgaat attgtgataa gttgaaagaa atgmacacag aaaggracag actcaaactc   1380
acttcctgga tattgattac aatttaggaa agagacttgg caatttatat gggcttttcc   1440
tcaaatcatg gatgtagtgt gttgcccctgt acaaaatgct ggctactaag tggaggaaac   1500
aaattgttct gtactcatat aaaaccatag tatgtccctt cctgaaaaac atttttcagt   1560
ttaacaattt tcatccttca agaaagacat gataagcaca aagcaaggag agtttgaaaa   1620
tatcagtgaa actcttggga ctcagtcaga aagagggaag gtgttaaatg atacatgaaa   1680
ttaattttc aaaaaatatt ggaatattgg gtgttgccct atgaagccaa aggtagaaaa   1740
aaattaagag aaatactgta ctgcccatca catgtgatca ttaacctagg aaatttatcc   1800
```

```
cagaatgtaa tctgggttga aaatctattg gtaaattttt tggataaatt cattgctggt    1860
attaagaagt ttttaggttt ttttttagtt cgacaagaaa gcttagggct ggtaaggtaa    1920
aataaggact gcactaaaac tttcagtagt gaagcctagc tgtgtgatct tgaacaagtt    1980
acttaacctt agtgccttgg ttttttaaat gctatctact tttctgggta atagtgacaa    2040
ctaaatgaaa ttttataatt ttacatatat aatatatatg taaatcgttg gacccatttg    2100
gctaataata ctatattagg atgaattgac tcatttgctc ttcatcacta gcctataaaa    2160
gaaatattac tactaatagt actaataata ctcctttctg aaataagacc tgggtatatg    2220
aagtcttgaa gccacttaat ctgcctggga agcagcttct cttgcagatg agatgatcat    2280
ccaattaggc cactgtatag gtttgtgaga atcatgtgag ttaattgatg gtaaagttat    2340
ttgaaaactg aagcattata aagtttaat gtaacatata taatccactt aatagataag    2400
aaaagtgagg ccctgtagac ccacaaataa cctaatcttt tgtgtttttt tgattttttt    2460
ttatatatat atatttgata tataaggt ggaaagattt ttatcttagt cttttaacat      2520
gaaaattctt ttacagctga gaaatttctt gaatctgttg aaggaaatca gaattatcca    2580
ctgttgcttt tgacattact ggagaagtcc caggataatg ttatcaaagt atgtgcttca    2640
gtaacattca aaaactatat taaaggaac tggagaattg taagtatttt gtgaatacat      2700
aatttaatac cctgtatgtt tataaggttt atataagcag tgttcttcaa agataaggca    2760
cgtgcttgta gtcccaacta ctctggaggc tgaggcggaa ggatcacttg agtccaggag    2820
ttcaaggctg cagtgagcta tgattgcacc actgtactct agccttttag tgacagaatg    2880
agaccttgtc tcaaaaaaaa ggattcagat atggatcaaa gataaaatta aacaggaccc    2940
ttttccaaag cttctgttat ttcatttgaa tttatataaa tttgtccagc ttcatacctc    3000
gggttgctag ggagtgagac ttggtcttaa tctccattat gtttggaatt tatgctttac    3060
tcaccrccta ctgaaaagac attgtgggaa gacagtctga ataatgaag tgatttctga     3120 tgttggaaaa ataaagctga gaagaaatca gatacataaa acatttgcag aatgcaaaat    3180
aatttagatt tcaacttttt gataaggtat tttgccctat gtcttgtggg atatgtatat    3240
atatactaat tttgagatta aacctatttt ataacaggtt taatgattag taaattataa    3300
attaagaaac aggcattttt tttccttagc ttaggacagt gattctcaac tgggggcagt    3360
ttggctcacc aggggacatt tggcagtata tttggagaca tcatagctgg aggattgcta    3420
ctggaatcta gtgggtaaag gccagagatg ctgctaagca tcctacaatg cacaagatag    3480 cttttccacaa caaagaatta tctgagccaa aatgtcagat tgagaaagcc tggctcatga   3540
tagagaaaaa gatgaggctt ttctatagtg atagcagtta tgatgttaca aagtattagc    3600
agttgacaaa aatcatcagt ttatctaaaa agtcaacttt aaactgctca aaaacatctt    3660
agagtcttac ttttttttctc attccataaa agagagagta aatattgttt taagcctgta   3720
tgatttctca agtatcacca tgagtggtaa agaaatctta gaggccgggc ttggtggccc    3780
atgcctgtaa tttcagcact tgggaggct gaggtgggtg gattgcttga gctcagcaat     3840
tcaagaccag cttgggcaat aaagtgagat cccatctttc aaaaaatac aaaaattagc     3900 gaggcatatg gtggtgcacg gcctgtagtc ccagccatta gggaggctga gatgagggga    3960
tcacttgtgc ctgggaggca gaggttgcaa tgaactgaga tggtgccact gcacttcagc    4020
ttgggcaaca gtgccagaca ctgtcttta aatctcagaa tgtttaaaag tccatctcta     4080
ctggtagaca tgccagccct ctccctctat tttgattgt aaaactagtg agacttaaca     4140
gaatctcttt gggtgatata atctaggatg cattctaact agtaatggtc aagaaatttt    4200
```

-continued

```
cacagagggc tgggtatggt ggctcacacc tgtaatccca gcactttagg aggctcagat    4260
gggaggattg cttgaggcca ggagttggag accagcctgg acaacaaagt gagacccctc    4320
ttctctacaa aaaatttaa aattagccag gtgtggtcgt gtgtggtgtg catctgtggt    4380
ccttgggagg ctgcagtggg agggattgtc ttgagtctgg gaggtgaagg ctgcagtgag    4440
ccaaggtttt gtgctaccct ccagcctggg tgacagatgg aaacccagtc tcaaaaaaaa    4500
aaaaagaata aaaaaattg gaaagatttt tgttctaaag tgagagttaa attgaagctt    4560
ttgaggatgt gtatggatta agtagcatat atctgtaaag attttaatta wgkgtcctga    4620
ttagtttaaa tatgaaatgg aaaaaaaawt tttttttttt tttttttttt tttttttttt    4680
tttttttttt tttgagaggg agtcttgctc tgttgcccag gctggaatgc aatggtgcga    4740
tcttggctca ttgcagcctc tgcctctcag gtccaaatga ttgtcctgcc tcagcctcct    4800
gagtagttag tgttacaggt gcccaccacc atgttcagct aattttgtat ttttagtaga    4860
aatggtttca ccatgttggc caggctggtc tcaaactcct gaccttgagt gagccatcgc    4920
acctggccta aaatgaaat ttttttttt ttttttttt gtangagaca gagtcactct    4980
wgttgcccag gctggagtgc agcggcacca tctcggctcc ctgcaacctc cacctcctgg    5040
gttcaagcaa ttctcctgct tcagcctccc gagtaactgg gattataggt gcctgccacc    5100
atgtccggct aattttttgta tgtttagtag agacatggtt tcaccatgtt ggtcaggctg    5160
gtctcaaact cctgacctca ggtgatccac ctgccttggc ctctcaaagt gctgggatta    5220
taggcgtgag ccactgcgcc cagtctaaaa tggaaattct taattggcat caaggagtaa    5280
gggaagttca ctaatttgta tgtaaaatat ttgcatttgg gaggcaatgt acgtttttct    5340
gggaaaagga ttcacgctgt catcagatta ttgaaggaat ctgtgaccca ttcatgtaga    5400
gggaaactga agaagacca aaccttcctc tatttgtttt cttagaaaat tagtaaataa    5460
aaaaacagtt atgttttacc taaaatcatg tggacatgaa tgtggatttt gtgttacttc    5520
ctcagttact gctttgcttt taggttgaag atgaaccaaa caaaatttgt gaagccgatc    5580
gagtggccat taaagccaac atagtgcact tgatgcttag cagcccagag caaattcaga    5640
agcaggtaat gtcgctccac ttttagatg ggctcctctg taaagctctg atctaattaa    5700
tcttttcctc tcctagttaa gtgatgcaat tagcattatt ggcagagaag attttccaca    5760
gaaatggcct gacttgctga cagaaatggt gaatcgcttt cagagtggag atttccatgt    5820
tattaatgga gtcctccgta cagcacattc attatttaaa aggtattgat gcatagattc    5880 atgttttttaa aatacttcct aaagttttat ttgcttgtgt aaacagttgt gttttttgtga    5940 ctgttgtcat tcctttgaat ctgatcatct tggaatgaga gcagaagttt ctgtatkgcg    6000
tttgtttctc ctcaactagg atgtttattt catattgctc tattacctgt gaaatactta    6060
gtcttgataa actgcttgat cccttttaaaa agaaaactgg ctgggcatga tggctcacac    6120
ctataatcct agcactttag gagggcaaag tgggcggatc acctgaggtc aggagtttga    6180
gaccagcctg gccaacatgg taaaacccg tctctactaa aaatacaaaa aaaactagcc    6240
aggcatggtg gtatgtgcct gtcatcccag ctactcagga ggctgagaca ggagaatcac    6300
ttgagcctgg gaggtggagg ctgcagtgag ccgagatcaa accactgcac tccagcctgg    6360
gcgacagagc gagactccgt ctcaaaaaaa aaaaaaaaa aaaaaaaaaa agaattccct    6420
ttgaatttcg gaatttcgga aacccatcta ttcatagatg tccaatcagc atctctcctt    6480
gaagacctaa agtgagtaaa taaaaaaaac ttgtaaattt atctgtttta ccttaatttt    6540
```

```
ttagataccg tcatgaattt aagtcaaacg agttatggac tgaaattaag cttgttctgg      6600
atgcctttgc tttgcctttg actaatcttt ttaaggtatg gaatgcatct tggtgatatt      6660
tttaaattaa tattttaaat tgcttgaatg tttgtataca tgttaagaga atgctttgaa      6720
agcttatttg ataaataatg tttagagcat ttcttttgaa aaatttcaaa cctacacaga      6780
aatagagatg ctatagtgaa ctcccatcta ttattcacaa aatttaatgg ttagcaacgt      6840
tttattttct ctgtccccctt tcttaggaat gttataaaag caaatcccaa gcatcatatc      6900
atttcaccca gtattttaa agtatgtgtc tctagaggaa gaaatacata tttttatttg        6960
actatgtttg gagtttaatt aattatatat ttatacatta ttttacagct ttacaggata      7020
ctttcctgaa tgtgttcttg gtgtttgtga aaatcctata agatttaaag aaatatatat      7080 atacttttt tcttttttct tttttaaaga cagggtctca ctctcattgc ccaggctgga        7140
gtgcagtggg gcatgattat agctcactgc agcctcaact acccaagctc aggtgattct      7200
cccacctcag cattccaagt agctgggact acaggtgcac actaccatgc ctggctgctt      7260
tttctctttt ttttttccctc tctcttttt tttttttttt tttttttttt gagatggagt      7320
ttcgctcttg ctcactgcaa cctccgcctc ccgggttcaa gcaattctcc gagtacactg      7380
ggattacagc ctgtgccact gggcctggcc agtaaaacct gttaatcgca tttagaataa      7440
taaagttgga aacaacctaa ataccaagtg gcagatgaat tgtttaataa gagcatataa      7500
agatagtttt gtgtaatata ttttatata tgcacagatt gggaagacgt agttcagaat        7560
attaacactg gactttttag tgccattatg aacagttcaa aaatacatac tttaacctat      7620
tttccacaat ctnttaagtg actgtattat ttaaaagcca aggctgggca tggtggctca      7680
cgcctgtaat cccagcactt tgagaggccg aggcgggcgg atcacgaggt caggagatcg      7740
agaccaccat ggctaacgtg gtgtcaggag atcgagacca ccatggctaa cgtggtgaaa      7800
ccccgtctct actaaaaata caaaaaacaa aaacaaaatt agccgggcgt ggtggcaggc      7860
acctatagtc ccagctactt gggaggctga ggcaggagaa tggtgtgaac ccaggaggtg      7920
gagcttgcag cgagccgaga ttgtgccact gcgctccagc ctggacgaca gagcaagact      7980
ccgtctcaaa aaaataaata agtaaaatat gaatagtctc agcttagtgc aaggctgttt      8040
cactaagatc agcatgctgg gtttatgatg cactaaaacc atgttgctaa attccttttcc      8100 aaggccacta ttgaactctg cagtacccat gcaaatgatg cctctgccct gaggattctg      8160
ttttcttccc tgatcctgat ctcaaaattg ttctatagtt taaactttca ggtaagttca      8220
tttgatttct tgcttttggt tcttactctt tgatttttaaa tagggttttc tttctgtttg      8280
ataaagactt ctttgccagc attgattttt ctgaaagaaa aggtttttc tgactctatt        8340 tatctatagt gttctgttct acagtagttc tttcagatgc taatgagatg tttcatggaa      8400
aaaagcagta ttctcttata tctagtaggt tagcaaaacc ccacatccta actcactctt      8460
ggagagtcac cctgtacact gttttactgg tggcattaag aagctagatt tctgaggcct      8520
tcctctttcg ttcatttata tgggtattaa catttgggga atcatgtttt ggttaggggt      8580
tgctgtccag cttatacaaa atgactttta ttggaagcca tatgagggag acaaaagact      8640
tgaagtacca gactttgaaa ggggtaggaa ctagtagtat ttcagaggaa acatacccac      8700
agggctatag caggaatgc ctagttaccc tgttgctact gagatagtgg cctccaatca       8760
ttctttctgt tcttaatcat taattcaaga ttcaggacca agaaaggggt gttaattggt      8820
acaaactgtt gctatactgc gatgcaagga agggcctagc ccattcattg tttgtagcca      8880
gtacctggac ttatcttcac aacatgaata aactcatagt ggtagggaaa gcattcccca      8940
```

```
aaaggaaatt gggttgtttt agctagaata ggagatgaac agcccaaaag gacatgtccc   9000
acatcagtgt tcagctggat agcagtttga gaagttctta cttaaatgag tactactatt   9060
tttgcttaca ccttttgaat tctgagaagt caggtttaat gaagctcttg agaacttgtc   9120
tggcagggag accaaggaaa gaggcataat ctaccctcag gggacttgta ccctcattaa   9180
gaaggcagta ctatgccaca agaaatcagt aactaaaaga caattagttt atctgccttg   9240
gtggtcatct acaataaac gtagttcaga aaagaaaggg gatgtattag tatgcactga    9300
gcttgagctt tgtaaggaaa gtcttcatat agtcttagct gaaccttgaa ggaagattta   9360
gattaggatg agaactagag gtggcatcat ttatagcata caaacagagg cagaagtcag   9420
aatgctttat gcagctgcca gatgtagctg agcagagaa ttcttgtcag aataggtaat    9480
gctcaggctg tgaagcctgt gtataaaatg ttttgtccac gtggtaaggg aacttataaa   9540
agtggtgttc ttaatatttt aatcaaaagt ttcaagtcag tgtttattct gtaggatctc   9600
cctgaatttt ttgaagataa tatggaaact tggatgaata attttcatac tctcttaaca   9660
ttggataata agcttttaca aactgatgta agtatttaaa atgtcgcctg agtggtcttt   9720
ttctttcatt aagagttatt tggctacagt ctggaaacct atttactctt gcattgttaa   9780
aagataaaat ttcaatactg taataatatt tgattctatt tgatgttaca tgtttggtgt   9840
gtgtagtata cagaattact cttatcatgg gcttggctta agccatagtg tacatataag   9900
gctgtttcat tacattattg aaagtaggtc tttaaagtag tgacattatg gatatttcat   9960
gaaataaaat tatttttcat tgaagatact aagaaaactt aaaactctat aatggtagcc  10020
cctttttaaa aatcatctgg ctaggcatgg tggttcacac ctgtaatccc agcactttgg  10080
gcggccaagg tggggaggat cccttgagcc caggagttca agaccagcct ggcaatgta   10140 aggagacccc catcactaca aaaataaaa ataaaattag ccagatgtgt tggctcatgc    10200
taatggtcac agctactcag aaggcttagt tgtgaggatc ccttgacctt gagcccagga  10260
gggcaaggct gcaatgagct gtgaccatgc cactgcactc cagcctggga gacagaggga  10320
gacctcgtct cagaaaaaga aaaattatc cacagctcga gaaagagaga aaatggtaaa    10380
agattgtaat ttgtaaatat ttctgatatg ggttttatat tgtgtacttt taaacatata  10440
acacttattc tgtgctactc atttgttaat atatttatga ccttctttcc gaagagacaa  10500
aagacaaaat attaaaaata tttcaatacc aaataaacta aaaattagaa ttggtgattc  10560 aaaatcaggtt ttaagagtgg ggtacagaaa gaaattgtta ctatcgttgt acaacagatt  10620
ttgtctcaga gtttgactat attaatagga actttaaaag atgtagctct cataaaataa  10680
ttatttcagt ccaatgggag ggaaaaacac tccttcagaa aacaaaactt ttcttcacac  10740
aaaagtcaca aggaaatttt ttggatagaa tcttacaagg acctttttgc ccagttaacc  10800
atgtgctacc ttgtgctact atttatgcct taagtaatca gtgtgaggga gttttggttt  10860
tggctttggt ttttgttctt actctgatgt cttcccttgt ctcactctgt caccaaggct  10920
ggagtgcagt ggcatgatca tgacttactg cagcttcgac ctccctgggc tcaagtgatc  10980
ctcccacctc agcctcccaa gtagcaggga ctatgggtat gcaccaccat gcccagctga  11040
ttttttttat tttgggggct tgctgtgttg cccaggctag actcaaaact cctgggcttg  11100
gcccgtcgca gtggcccacg cctataatcc cagcactttg ggaggccgag gccatcctgg  11160
ctaacacggt gaaaccccgt ctctactaaa aaaaaaaat acaaaaatta gccgggcgtg  11220
atggcgggtg cctgtagtcc cagctacttg ggaggcctga ggcaggagaa tgacgtgaac  11280
```

-continued

```
ccaggaggcg gagcttgcag tgagctgaga tcgcgccact gcactccagc ctgggcaaca    11340
gagggagact gcgtctcaaa aaaaaaaaa aaaaaccact cctggcctca ggccatcctc    11400
cagcctcagc ctcccagagg gttgggatta ccggcgtgag ccactacact cagccagaat    11460
atactgtttg aatctaatac ggaaatattt tgtaattcag caacttattt gaaagacttg    11520
gtgaaaagat tggtggtggc atagctgtag tttacaataa ctgatttgat ttggatttaa    11580
ttgataaaga gtctagttca ggaatttcag ttactcctct tacttatgtt agcattagag    11640
ttgtatgttg gagttttgt tttcttttat gtgaggatga agaggaagcc ggcttattgg    11700
agctcttaaa atcccagatt tgtgataatg ccgcactcta tgcacaaaag tacgatgaag    11760
aattccagcg atacctgcct cgttttgtta cagccatctg gaatttacta gttcaacgg    11820 gtcaagaggt taaatatgat ttggtaagat gatggtggag acaaataatt aaaagacatt    11880
ctctccctat ctcctccaag aaataagctg ttgagttttg cttttaaaaa tattcttgtt    11940
tttgtgtttt gttccagttg gtaagtaatg caattcaatt tctggcttca gtttgtgaga    12000
gacctcatta taagaatcta tttgaggacc agaacacgct gacaagtatc tgtgaaaagg    12060
ttattgtgcc taacatggaa tttagaggta attatggcaa aagtatatta gtataaatct    12120
actaagtctg tgtttgtttt ttgtaacata ttcagtctaa ttcatttatt actggataaa    12180
acttgtatgt catctatttc ttattttcta aaccaagaca gaaaatgtag tatctgtaat    12240
gagttttgtt gtgccctgtg agggttttct catggaaata ttaaataaaa cttcaaaaat    12300
tcctttacac taaaaaaata aactatctgg aatttctatt tagagaaaga atttgatttt    12360
gtttcattta ttatttcaat gaattttag ctggctttat ttatttatat atttatttga    12420 gacagggtc tcgctctgtc acccaggctg gagtgcagtg atgcaatctt ggctcactgc    12480
aaccttagcc tcccaggctc aagtgatcct cctacctcag tcttctgagt agctgggacc    12540
acaggcacac atcaccatgc ctggctaatt tcttgtattt ttggtagaga cagggtt    12597
```

<210> SEQ ID NO 13
<211> LENGTH: 5037
<212> TYPE: DNA
<213> ORGANISM: Homo sapiens
<220> FEATURE:
<223> OTHER INFORMATION:
<221> NAME/KEY: unsure
<222> LOCATION: 801
<223> OTHER INFORMATION: unknown

<400> SEQUENCE: 13

```
gagagagaga gggagtctcg ctctgtctcc caggctggag tgcagtggca tgattttggc      60
tcactgcaac ctccacttcc caggttcaag cgattctcaa gcctcagcct cccgagtagc     120
tgggactaca gatgtgcacc acatacctgg ctaattttgc tattttaat ggagatgggt     180 tttgccatgt tagccaggtt ggtctcagac tctagcctca agtgatccgc cagcctcggc     240
ctcccaaagt gctggggtta caggtgtgag ccaccaagca tggcctctgc tactgatttc     300
taagagaaag agaccccaaa cagttctctc tcagactcac ctgctccatt catgtcagct     360
cactgtttct tcctcttagt caacctcttt aattattttt taaaccttga gccttctaga     420
aatactcagt atttcccagc taaattttgt tgccaacccg tcctaatttt aaaaggaagg     480
gaaatttaga ttattttaa atgtagagag ctatctcggg gttgtctaag catcttaaaa     540
tttagttgat gaattagtgc gctttttcc ccccagtcgc tctcttattc tgaagtttaa     600
ctaaactcta tttgtttttg ctgttttgt attttacagc tatcatgaga agttttctc     660
```

```
tcctacaaga agccataatc ccctacatcc ctactctcat cactcagctt acacagaagc    720
tattagctgt tagtaaggta atagagccaa ttttgaaagt ggggttcctt ttttatttgc    780
tccaaactgt ttgggcctca naactctttg gcattacgtg aagctttaga gaaggtctgt    840
gaattcttcc tgaccagcca ctaatggact tttctgaaag tgtgggcatg ctgttagatt    900
ggagacgtaa tagcagtcac ctttaagtgt gtgctagaag cttgaataca ttttcattct    960
cattacaaaa gtaacatgtt tattgtagaa aaagaaagtg cagatgatcc aaaattacct   1020
taaatggagt taagtaggct ttgcactaaa tggatataaa agaggctgtc tggacttcta   1080
tgaaatgatg attaaaatcc tttgtgttgt cttttcttcc ttactcttat ttctcaaaag   1140
gaaagttcac tctgatcaaa attttacaga tacttagatt catgtttatt aacactaaat   1200
tttagaaaat aaatccgttt aaggctgaca gaattccttt ttagatgcta ttcttgatct   1260
tatgagaatt agatcaattc ataggaagtg ttggagggat tttggagaac agagtgatta   1320
ttattcaacc gagttagggc taaagggtct ttggactacc ttagggcctt gagggatgga   1380
gcggggaggg aacccaagtc tccgcctccc atatgtatta ccatctcatg ttctgattga   1440
gttagatttg tatgctagta gccttccaag aacttgttta aagaaaatg ggttttgtt   1500 gcttaaaaag aacataaaaa actactcatt tggggatta tcagtaagta gacatagaca   1560
ttgaggccca cagaagttaa ggctagtggc attactagga cttagtattt cttctctgcg   1620
agggcacgtg ggcttaagac aagttacagc tctgggatct gaggtttgta taagcaactc   1680
tgtaactctg aagtattttt ttcatggtgg actttgggcc atttaaaaaa aaattcaaat   1740
gaacaagcac tagggtataa ttggtgtttt tttcttaatt ttgattttta aaaaataaga   1800
tggcctctat tttaaatgtg ttttataaag gttaggtgtg gattattagc ataattaggt   1860
tttttttttt taatttcaga acccaagcaa acctcacttt aatcactaca tgtttgaagc   1920
aatatgttta tccataagaa taacttgcaa agctaaccct gctgctgttg taaattttga   1980
ggaggctttg ttttggtgt ttactgaaat cttacaaaat gatgtgcaag gtaagttaac   2040
ggaaattatt ttcttgtaa tggaataaaa ttaacatggc tataaaatgc agcccaccta   2100
agcgatgtgg gccttttgtg tcagtcattc cttctgaagc tcacagctct gttttactt   2160 ttatcaacag aatttattcc atacgtcttt caagtgatgt ctttgcttct ggaaacacac   2220
aaaaatgaca tcccgtcttc ctatatggcc ttatttcctc atctccttca gccagtgctt   2280
tgggaaagaa caggaaatat tcctgctcta gtgaggcttc ttcaagcatt cttagaacgc   2340
ggttcaaaca caatagcaag tgctgcagct gacaaaattg tgcgtcaggt tttgatataa   2400
ctgtaatttt ataaagtagc ttggagaaac tggggatggc agatgtttga aattttttta   2460
tttaaaataa atttaaggct ggggggcagtg gctcaagccc accactttgg gagcctctag   2520
tgggaggatc ccttgagccg aggagtttaa gaccagccta gcaacgtgg tgagatctat   2580 ctctacaaag gaaaaaaag cttttttaatt agttggacac agtggagcat gcctgtggtc   2640
ccatctactt gggaggctaa ggtgagaggg tcgcttgagc ccaggagttt aaggctgcag   2700
tgagccatga tctcaccatt gcactccatc ctgggcaaca gagctagacc ctgtctctta   2760
aaaaaaataa taataataat aacgaaaata attagtagaa aatgttatgg tatgtttttat   2820 cagaattctg tatcctttac ttatttatat ccatgatgga aaattttaaa aacagagcca   2880
aacaggttga tttaaaaac ttaactttgg tcgggcgtgg tggctcacac ctgtaatctc   2940
agcactttgg gaggccgagg tgggcagatc acctgaggtc aggagttcaa gaccagcctg   3000
gccaacatgg cgaaaccccg tctctactaa aaataaaaat tacgtgggtg tggtggcacg   3060
```

```
tgcctgtaat cccagctact cagaaggctg aggcaggaga atcgcttgaa cctgggaagc    3120
agaggttgca gtgagccaag atcgccccat tgcactctag cctgggcaac aagagtgaaa    3180
ctccgtctca agaaaaaaa aaattacttt aatggctacg cgggaggaat tgttccccat    3240
atgtttcaga ataattaaa gagaaaagga tagattatta cagtatgaac tctgttttaa    3300
gacatatatc atgtttaact tttcgaataa ttattcctgt taaccatttt ctgttggatc    3360
tcatttctta acagcctggg ttactaggtg tctttcagaa gctgattgca tccaaagcaa    3420
atgaccacca aggtttttat cttctaaaca gtataataga gcacatgcct ccgtgagtat    3480
gactagaact ttgtgcattt atttagaaat tttgttaggt gctcagaaaa gtcctaaatt    3540
tatattgttg attttttta attctttagt gaatcagttg accaatatag gaaacaaatc    3600
ttcattctgc tattccagag acttcagaat tccaaaacaa ccaagtttat caagagtaag    3660
taaaatcatc tggatgttct acagaagtaa tgaagaagg tagctaaaac ccttagactt    3720
tatggttgca gatacatttt ttatccgttt taaactttat gcaaaaaata cttggccacg    3780
tgtggaggtt catgcctgta atcgcagcac tttgggtggc caaggaggc cgatcgcttg    3840
agctcaggag ttcaagacca gcctgggcaa catggcgaaa ccctgtccct acgaaaagta    3900
caacaaaatt agccaggcat ggtggcatgt gcctgtagtt gcagctgctt gggaggctga    3960
agtaggagca ttacctaagt cccagaggtt gaggctgcag tgagccaaga ttacacccac    4020
tgcactccat cctaggtgat agagtgagac cctgtctcaa aaaaaaaaa gaaatattg    4080
taagggcctg gtgcagtggc tcttatttgt aatcccagca ctttgggagg tgaaagtggg    4140
agtattcctt gagttcagga gttaacgacc agcctgggca acatggtaag accctgtctc    4200
tacaaaacag ccaagcatgg tggtgtgtgc ctgtagcccc agctactcag gaggctgagg    4260
tgggaggatc acttgaccct gggaagttaa ggctgcgtga gctgtgatca cgctcctgca    4320
cccagcctag gtgatagagt gaaaccttct cacaagaaaa aagaaaatat tttaagatgt    4380
ttgtgttctc caaacattaa gttagtgtta gtcatattgt gttccagagg ttggtttatg    4440
gttggatacc aaaacatttt ttcagtagag agaatattat aaggaaatat aaatcaaaga    4500
gagacagcat gtaaaggtct atgacagaaa gacaagtttt ctatttacta gaaggcaggt    4560
attgatgcca cagcctttgg atgttaatga ttaagcatag gtttattttg cagacttatc    4620
agttaccagt ttagtgcgtg agttctctat gctgatattc tgcatcttct ttcaacaggt    4680
ttttttagtct ttattaattt gtattgcata aaatatgggg cactagcact acaagaaata    4740
tttgatggta tacaaccaaa gtaagtttgt tttattatt ttttaagggg aagaaaatg    4800
ttttgacttt tttttagta caaatcagta tctctgtctt atagatgatg atgtggttct    4860
tggtatggag atagtgtcta tggttttcaa aatattctta ggtattggga gtaaagaaaa    4920
agtaatcctg gcccagccat ggtggctcac gcccgtaatc ccacactctg agaggctgag    4980
gagggcggat ttagctcagg agtttgagac cagcctgggc aatataagtg agactcc       5037
```

<210> SEQ ID NO 14
<211> LENGTH: 1919
<212> TYPE: DNA
<213> ORGANISM: Homo sapiens
<220> FEATURE:
<223> OTHER INFORMATION:
<221> NAME/KEY: unsure
<222> LOCATION: 1015
<223> OTHER INFORMATION: unknown
<221> NAME/KEY: unsure
<222> LOCATION: 1824

<223> OTHER INFORMATION: unknown
<221> NAME/KEY: CDS
<222> LOCATION: (97)...(684)

<400> SEQUENCE: 14

```
gtgaggcgga gcggcggcag gagcgggtag tgccagctac ggtccgcggc tggggttccc      60
tcctccgttt ctgtatcccc acgagatcct atagca atg gaa ctc agc gat gca      114
                                        Met Glu Leu Ser Asp Ala
                                         1               5 aat ctg caa aca cta aca gaa tat tta aag aaa aca ctt gat cct gat      162
Asn Leu Gln Thr Leu Thr Glu Tyr Leu Lys Lys Thr Leu Asp Pro Asp
             10                  15                  20 cct gcc atc cga cgt cca gct gag aaa ttt ctt gaa tct gtt gaa gga      210
Pro Ala Ile Arg Arg Pro Ala Glu Lys Phe Leu Glu Ser Val Glu Gly
         25                  30                  35 aat cag aat tat cca ctg ttg ctt ttg aca tta ctg gag aag tcc cag      258
Asn Gln Asn Tyr Pro Leu Leu Leu Leu Thr Leu Leu Glu Lys Ser Gln
     40                  45                  50 gat aat gtt atc aaa gta tgt gct tca gta aca ttc aaa aac tat att      306
Asp Asn Val Ile Lys Val Cys Ala Ser Val Thr Phe Lys Asn Tyr Ile
 55                  60                  65                  70 aaa agg aac tgg aga att gtt gaa gat gaa cca aac aaa att tgt gaa      354
Lys Arg Asn Trp Arg Ile Val Glu Asp Glu Pro Asn Lys Ile Cys Glu
                 75                  80                  85 gcc gat cga gtg gcc att aaa gcc aac ata gtg cac ttg atg ctt agc      402
Ala Asp Arg Val Ala Ile Lys Ala Asn Ile Val His Leu Met Leu Ser
             90                  95                 100 agc cca gag caa att cag aag cag tta agt gat gca att agc att att      450
Ser Pro Glu Gln Ile Gln Lys Gln Leu Ser Asp Ala Ile Ser Ile Ile
        105                 110                 115 ggc aga gaa gat ttt cca cag aaa tgg cct gac ttg ctg aca gaa atg      498
Gly Arg Glu Asp Phe Pro Gln Lys Trp Pro Asp Leu Leu Thr Glu Met
    120                 125                 130 gtg aat cgc ttt cag agt gga gat ttc cat gtt att aat gga gtc ctc      546
Val Asn Arg Phe Gln Ser Gly Asp Phe His Val Ile Asn Gly Val Leu
135                 140                 145                 150 cgt aca gca cat tca tta ttt aaa aga tac cgt cat gaa ttt aag tca      594
Arg Thr Ala His Ser Leu Phe Lys Arg Tyr Arg His Glu Phe Lys Ser
                155                 160                 165 aac gag tta tgg act gaa att aag ctt gtt ctg gat gcc ttt gct ttg      642
Asn Glu Leu Trp Thr Glu Ile Lys Leu Val Leu Asp Ala Phe Ala Leu
            170                 175                 180 cct ttg act aat ctt ttt aag gta tgg aat gca tct tgg tga tatttttaaa  694
Pro Leu Thr Asn Leu Phe Lys Val Trp Asn Ala Ser Trp
        185                 190                 195 ttaatatttt aaattgcttg aatgtttgta tacatgttaa gagaatgctt tgaaagctta    754
tttgatagat aatgtttaga gcatttcttt tgaaaaattt caaacctaca cagaaataga    814
gatgctatag tgaactccca tctattatta cacaaattta atggttagca acgtttttatt  874 ttctctgttc cctttcttag gaatgttata aaagcaaatc ccaagcatca tatcatttca    934
cccaagtatt ttaaagtatg tgtctctaaa ggaagaaata catattttta tttgactatg    994
tttggagttt aattaattat ntatttatac attattttac agtttacagg atactttcct  1054
gaatgtgttc ttggtgtttg tgaaaatcct ataagattaa agaaatatat atatacttt   1114 tttctttttt cttttttaaa gacagggtct cactctcatt gcccaggctg gagtgcagtg  1174
agctattaca gtgccactgc aatccagcct gggcaacaga gcgaggtccc gtttcttaaa  1234
aaacatatat gtgtgtggcg tgtgtatata tatgtatata tatttttttca ttgtattatt 1294
```

-continued

```
gcggagactt tcaaacatat atagaaagag cataatgaag cctgcatgtg cccagcttca    1354
ataattacca atatcttgcc agttttgttt cgtttctcct ttgattctct gtattgagca    1414
agtcttagac atcatacgtt tcccgcgtaa gtaccttatt ctacatcatt aaccagtaag    1474 gacttttttaa ttaaccacaa taccactatc acacctaata atagtaattc cttatggatc   1534
ttttctttag acctattttt gaaggcataa aagcagttga gtttctggag aattttttgga   1594 tggtgattaa tgacttgact ggctgctctt cccagagctg tggcagctct cccccccgtag  1654 aagatggggt ttgtattggc gcaccaagat ctccaacagc cagtgtgtgt ttcccatttc    1714
ctgtaggttc catcaatggt gagcaccagc ctgaatgcag aagcgctcca gtatctccaa    1774
gggtaccttc aggcagccag tgtgacactg ctttaaactg cattttttctn aatgggctaa   1834 acccagatgg tttcctagga aatcacaggc ttctgagcac agctgcatta aaacaaagga    1894
agttttcctt ttgaacttgt cacga                                          1919
```

<210> SEQ ID NO 15
<211> LENGTH: 1418
<212> TYPE: DNA
<213> ORGANISM: Homo sapiens
<220> FEATURE:
<223> OTHER INFORMATION:
<221> NAME/KEY: unsure
<222> LOCATION: 1205
<223> OTHER INFORMATION: unknown
<221> NAME/KEY: CDS
<222> LOCATION: (71)...(637)

<400> SEQUENCE: 15

```
tcagaagctg attgcatcca aagcaaatga ccaccaaggt ttttatcttc taaacagtat    60
aatagagcac atg cct cct gaa tca gtt gac caa tat agg aaa caa atc      109
             Met Pro Pro Glu Ser Val Asp Gln Tyr Arg Lys Gln Ile
               1               5                  10 ttc att ctg cta ttc cag aga ctt cag aat tcc aaa aca acc aag ttt    157
Phe Ile Leu Leu Phe Gln Arg Leu Gln Asn Ser Lys Thr Thr Lys Phe
 15                  20                  25 atc aag agt ttt tta gtc ttt att aat ttg tat tgc ata aaa tat ggg    205
Ile Lys Ser Phe Leu Val Phe Ile Asn Leu Tyr Cys Ile Lys Tyr Gly
 30                  35                  40                  45 gca cta gca cta caa gaa ata ttt gat ggt ata caa cca aaa atg ttt    253
Ala Leu Ala Leu Gln Glu Ile Phe Asp Gly Ile Gln Pro Lys Met Phe
                 50                  55                  60 gga atg gtt ttg gaa aaa att att att cct gaa att cag aag gta tct    301
Gly Met Val Leu Glu Lys Ile Ile Ile Pro Glu Ile Gln Lys Val Ser
 65                  70                  75 gga aat gta gag aaa aag atc tgt gcg gtt ggc ata acc aaa tta cta    349
Gly Asn Val Glu Lys Lys Ile Cys Ala Val Gly Ile Thr Lys Leu Leu
 80                  85                  90 aca gaa tgt ccc cca atg atg gac act gag tat acc aaa ctg tgg act    397
Thr Glu Cys Pro Pro Met Met Asp Thr Glu Tyr Thr Lys Leu Trp Thr
 95                 100                 105 cca tta tta cag tct ttg att ggt ctt ttt gag tta ccc gaa gat gat    445
Pro Leu Leu Gln Ser Leu Ile Gly Leu Phe Glu Leu Pro Glu Asp Asp
110                 115                 120                 125 acc att cct gat gag gaa cat ttt att gac ata gaa gat aca cca gga    493
Thr Ile Pro Asp Glu Glu His Phe Ile Asp Ile Glu Asp Thr Pro Gly
                130                 135                 140 tat cag act gcc ttc tca cag ttg gca ttt gct ggg aaa aaa gag cat    541
Tyr Gln Thr Ala Phe Ser Gln Leu Ala Phe Ala Gly Lys Lys Glu His
                145                 150                 155
```

| | | | | | | | | | | | | | | | |
|---|---|---|---|---|---|---|---|---|---|---|---|---|---|---|---|
|gat|cct|gta|ggt|caa|atg|gtg|aat|aac|ccc|aaa|att|cac|ctg|gca|cag|
|Asp|Pro|Val|Gly|Gln|Met|Val|Asn|Asn|Pro|Lys|Ile|His|Leu|Ala|Gln|
| | |160| | | |165| | | |170| | | | | |

589

| | | | | | | | | | | | | | | |
|---|---|---|---|---|---|---|---|---|---|---|---|---|---|---|
|tca|ctt|cac|aag|ttg|tct|acc|gcc|tgt|cca|gga|agg|acc|tat|ttt|tga|
|Ser|Leu|His|Lys|Leu|Ser|Thr|Ala|Cys|Pro|Gly|Arg|Thr|Tyr|Phe| |
| |175| | | | |180| | | | |185| | | | |

637

| | | | |
|---|---|---|---|
|aggcataaaa|gcagttgagt|ttctggagaaa|tttttggatg gtgattaatg acttgactgg|697|
|ctgctcttcc|cagagctgtg|gcagctctcc|cgtagaagat ggggttttgta ttggcgcacc|757|
|aagatctcca|acagccagtg|tgtgtttccc|atctcttgta ggttccatca atggtgagca|817|
|ccagcctgaa|tgcagaagcg|ctccagtatc|tccagggta ccttcaggca gccagtgtga|877|
|cactgcttta|aactgcattt|ttctaatggg|ctaaacccag atggtttcct aggaaatcac|937|
|aggcttctga|gcacagctgc|attaaaacaa|aggaagttct ccttttgaac ttgtcacgaa|997|
|ttccatcttg|taaaggatat|taaatgttgc|tttaacctga accttgagca aattagttgg|1057|
|tttgtgtgat|catacagtta|tgtgggtggc|ttctagtttg caacttcaag ggacaagtat|1117|
|taatagttca|gtgtatggcg|ttggtttgtg|ttgagcgttt gcacggtttg gataatctta|1177|
|aattttgacg|gacactgtgg|agactttnct|gttactaaat ccttttgttt tgaagctgtt|1237|
|gctatttgta|tttctcttgt|cctttatatt|ttttgtctgt ttatttacgc ttttattgga|1297|
|aatgtgaata|agtaaagaat|tacttgtgtt|acttgccaag cagtgcacat ttcatagttt|1357|
|caaatctgta|atcagcaata|aaaatcctaa|aatatgtacc taaaaaaaaa aaaaaaaaa|1417|
|a| | | |1418|

<210> SEQ ID NO 16
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 16
ggaagaataa tacttgtgca                                         20

<210> SEQ ID NO 17
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 17
tcccagcact ttgggaggct                                         20

<210> SEQ ID NO 18
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 18
cgaggtatga agctggacaa                                         20

<210> SEQ ID NO 19
<211> LENGTH: 20
<212> TYPE: DNA
<213> ORGANISM: Artificial Sequence
<220> FEATURE:

-continued

<223> OTHER INFORMATION: Antisense Oligonucleotide

<400> SEQUENCE: 19
atgtctccaa atatactgcc         20

<210> SEQ ID NO 20
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 20
gcgacattac ctgcttctga         20

<210> SEQ ID NO 21
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 21
tgaaataaac atcctagttg         20

<210> SEQ ID NO 22
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 22
cagggagatc ctacagaata         20

<210> SEQ ID NO 23
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 23
ggaataaatt ctgttgataa         20

<210> SEQ ID NO 24
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 24
aaccccggca aaatggcgcg         20

<210> SEQ ID NO 25
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 25
aaccccagcc gcggaccgta         20

```
<210> SEQ ID NO 26
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 26
ctgagttcca ttgctatagg                                                 20

<210> SEQ ID NO 27
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 27
agaaatttct cagctggacg                                                 20

<210> SEQ ID NO 28
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 28
attctgattt ccttcaacag                                                 20

<210> SEQ ID NO 29
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 29
atgtcaaaag caacagtgga                                                 20

<210> SEQ ID NO 30
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 30
tcctgggact tctccagtaa                                                 20

<210> SEQ ID NO 31
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 31
aatggccact cgatcggctt                                                 20

<210> SEQ ID NO 32
<211> LENGTH: 20
<212> TYPE: DNA
<213> ORGANISM: Artificial Sequence
<220> FEATURE:
<223> OTHER INFORMATION: Antisense Oligonucleotide
```

```
<400> SEQUENCE: 32
tctgggctgc taagcatcaa                                                    20

<210> SEQ ID NO 33
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 33
catcacttaa ctgcttctga                                                    20

<210> SEQ ID NO 34
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 34
ctgtggaaaa tcttctctgc                                                    20

<210> SEQ ID NO 35
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 35
gtcaggccat ttctgtggaa                                                    20

<210> SEQ ID NO 36
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 36
tgtcagcaag tcaggccatt                                                    20

<210> SEQ ID NO 37
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 37
aatgtgctgt acggaggact                                                    20

<210> SEQ ID NO 38
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 38
atgacggtat cttttaaata                                                    20

<210> SEQ ID NO 39
<211> LENGTH: 20
```

```
<212> TYPE: DNA
<213> ORGANISM: Artificial Sequence
<220> FEATURE:
<223> OTHER INFORMATION: Antisense Oligonucleotide

<400> SEQUENCE: 39
atagtggcct taaaaagatt                                              20

<210> SEQ ID NO 40
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 40
cagagttcaa tagtggcctt                                              20

<210> SEQ ID NO 41
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 41
aagtttccat attaccttcc                                              20

<210> SEQ ID NO 42
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 42
tccaagtttc catattacct                                              20

<210> SEQ ID NO 43
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 43
gaaattattc atccaagttt                                              20

<210> SEQ ID NO 44
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 44
gctccaataa gccggcttcc                                              20

<210> SEQ ID NO 45
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 45
```

-continued

```
cacaaatctg ggattttaag                                                      20

<210> SEQ ID NO 46
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 46
gccagaaatt gaattgcatt                                                      20

<210> SEQ ID NO 47
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 47
gttctggtcc tcaaatagat                                                      20

<210> SEQ ID NO 48
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 48
cagctctaaa ttccatgtta                                                      20

<210> SEQ ID NO 49
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 49
attcctgtca caggtccctc                                                      20

<210> SEQ ID NO 50
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 50
tattcctgca gcatggaatt                                                      20

<210> SEQ ID NO 51
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 51
actaggtaga tggctgcatc                                                      20

<210> SEQ ID NO 52
<211> LENGTH: 20
<212> TYPE: DNA
<213> ORGANISM: Artificial Sequence
```

```
<220> FEATURE:
<223> OTHER INFORMATION: Antisense Oligonucleotide

<400> SEQUENCE: 52
ataccgtcag ctttaaggac                                               20

<210> SEQ ID NO 53
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 53
tgaagatgat taatcaagag                                               20

<210> SEQ ID NO 54
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 54
gagctttgaa aagtttgtt                                                20

<210> SEQ ID NO 55
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 55
ctcatgatag ctttcataat                                               20

<210> SEQ ID NO 56
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 56
tcttactaac agctaatagc                                               20

<210> SEQ ID NO 57
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 57
gcaagttatt cttatggata                                               20

<210> SEQ ID NO 58
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 58
aacagcagca gggttagctt                                               20
```

```
<210> SEQ ID NO 59
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 59
tccaaacatt tttggttgta                                              20

<210> SEQ ID NO 60
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 60
agtaatttgg ttatgccaac                                              20

<210> SEQ ID NO 61
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 61
acattctgtt agtaatttgg                                              20

<210> SEQ ID NO 62
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 62
tggtgtatct tctatgtcaa                                              20

<210> SEQ ID NO 63
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 63
ttgtgaagtg actgtgccag                                              20

<210> SEQ ID NO 64
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 64
tagacaactt gtgaagtgac                                              20

<210> SEQ ID NO 65
<211> LENGTH: 20
<212> TYPE: DNA
<213> ORGANISM: Artificial Sequence
<220> FEATURE:
<223> OTHER INFORMATION: Antisense Oligonucleotide
```

```
<400> SEQUENCE: 65
attgatggaa cccttcctgg                                              20

<210> SEQ ID NO 66
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 66
actggagcgc ttctgcattc                                              20

<210> SEQ ID NO 67
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 67
atactggagc gcttctgcat                                              20

<210> SEQ ID NO 68
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 68
aatgcagttt aaagcagtgt                                              20

<210> SEQ ID NO 69
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 69
taatgcagct gtgctcagaa                                              20

<210> SEQ ID NO 70
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 70
agcaacattt aatatccttt                                              20

<210> SEQ ID NO 71
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 71
aaggttcagg ttaaagcaac                                              20

<210> SEQ ID NO 72
```

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 72
acacaaacca actaatttgc                                               20

<210> SEQ ID NO 73
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 73
gaagccaccc acataactgt                                               20

<210> SEQ ID NO 74
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 74
tagaagccac ccacataact                                               20

<210> SEQ ID NO 75
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 75
gtgcaaacgc tcaacacaaa                                               20

<210> SEQ ID NO 76
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 76
cgtcaaaatt taagattatc                                               20

<210> SEQ ID NO 77
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 77
tgcactgctt ggcaagtaac                                               20

<210> SEQ ID NO 78
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 78
```
agatttgaaa ctatgaaatg                                            20

<210> SEQ ID NO 79
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 79
ctgattacag atttgaaact                                            20

<210> SEQ ID NO 80
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 80
taggattttt attgctgatt                                            20

<210> SEQ ID NO 81
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 81
gcattccata ccttaaaaag                                            20

<210> SEQ ID NO 82
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 82
aagtccttac tggttaatga                                            20

<210> SEQ ID NO 83
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 83
ggagatcttg gtgcgccaat                                            20

<210> SEQ ID NO 84
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 84
ccattgatgg aacctacagg                                            20

<210> SEQ ID NO 85
<211> LENGTH: 20
<212> TYPE: DNA

-continued

```
<213> ORGANISM: Artificial Sequence
<220> FEATURE:
<223> OTHER INFORMATION: Antisense Oligonucleotide

<400> SEQUENCE: 85
atgccttcaa aaataggtcc                                              20

<210> SEQ ID NO 86
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 86
gatggaacct acaagagatg                                              20
```